United States Patent
Matsunaga et al.

(10) Patent No.: US 11,295,443 B2
(45) Date of Patent: Apr. 5, 2022

(54) IDENTIFICATION APPARATUS, IDENTIFIER TRAINING METHOD, IDENTIFICATION METHOD, AND RECORDING MEDIUM

(71) Applicant: CASIO COMPUTER CO., LTD., Tokyo (JP)

(72) Inventors: Kazuhisa Matsunaga, Fussa (JP); Mitsuyasu Nakajima, Mizuho-machi (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 104 days.

(21) Appl. No.: 16/823,919

(22) Filed: Mar. 19, 2020

(65) Prior Publication Data

US 2021/0248738 A1 Aug. 12, 2021

(30) Foreign Application Priority Data

Feb. 7, 2020 (JP) .............................. JP2020-019275

(51) Int. Cl.
*G06T 7/00* (2017.01)
*G06T 7/90* (2017.01)
(Continued)

(52) U.S. Cl.
CPC .......... *G06T 7/0012* (2013.01); *A61B 5/0075* (2013.01); *A61B 5/1032* (2013.01);
(Continued)

(58) Field of Classification Search
None
See application file for complete search history.

(56) References Cited

U.S. PATENT DOCUMENTS 6,069,689 A  5/2000 Zeng et al.
6,427,082 B1 7/2002 Nordstrom et al.
(Continued)

FOREIGN PATENT DOCUMENTS

JP  2004215738 A  8/2004
JP  2011033612 A  2/2011
(Continued)

OTHER PUBLICATIONS

Machine translation of JP-2018202044-A (Year: 2018).*
(Continued)

*Primary Examiner* — Vu Le
*Assistant Examiner* — Courtney Joan Nelson
(74) *Attorney, Agent, or Firm* — Holtz, Holtz & Volek PC

(57) ABSTRACT

An identification apparatus includes a processor and a memory configured to store a program to be executed by the processor. The processor acquires first image data obtained by capturing of an image of an affected area included in a skin or a mucosa by receiving first reception light. The first reception light is reflection light reflected from the affected area irradiated with first irradiation light including white light. The processor further acquires second image data obtained by capturing of an image of the affected area by receiving second reception light. The second reception light is light including light generated by fluorescent reaction in the affected area irradiated with second irradiation light. The second irradiation light includes light that allows the affected area to show fluorescent reaction when the affected area is irradiated with the light. The processor identifies the affected area based on the first image data and the second image data.

15 Claims, 15 Drawing Sheets

(51) Int. Cl.
*G06N 20/00* (2019.01)
*A61B 5/00* (2006.01)
*A61B 5/103* (2006.01)
*G06K 9/46* (2006.01)

(52) U.S. Cl.
CPC ............ *A61B 5/445* (2013.01); *G06K 9/4652* (2013.01); *G06N 20/00* (2019.01); *G06T 7/90* (2017.01); *G06T 2207/30088* (2013.01); *G06T 2207/30201* (2013.01)

(56) References Cited

U.S. PATENT DOCUMENTS

| | | | |
|---|---|---|---|
| 7,127,282 B2* | 10/2006 | Nordstrom | A61B 5/0071 600/477 |
| 10,456,009 B2 | 10/2019 | Kamiyama et al. | |
| 2008/0194969 A1 | 8/2008 | Werahera et al. | |
| 2013/0345544 A1 | 12/2013 | Werahera et al. | |
| 2016/0275675 A1 | 9/2016 | Nakajima | |
| 2016/0275681 A1* | 9/2016 | D'Alessandro | G06T 7/0016 |
| 2018/0310872 A1 | 11/2018 | Tseng et al. | |
| 2018/0360320 A1 | 12/2018 | Werahera et al. | |

FOREIGN PATENT DOCUMENTS

| | | | |
|---|---|---|---|
| JP | 2017045341 A | | 3/2017 |
| JP | 2018152106 A | | 9/2018 |
| JP | 2018202044 A | * | 12/2018 |
| WO | 2006119431 A2 | | 11/2006 |
| WO | 2016185617 A1 | | 11/2016 |
| WO | 2020008834 A1 | | 1/2020 |

OTHER PUBLICATIONS

Extended European Search Report (EESR) dated Oct. 2, 2020 issued in European Patent Application No. 20165331.8.
Australian Office Action dated Mar. 29, 2021 issued in counterpart Australian Application No. 2020202082.
Japanese Office Action (and English language translation thereof) dated Oct. 26, 2021 issued in counterpart Japanese Application No. 2020-019275.

* cited by examiner

FIG. 14

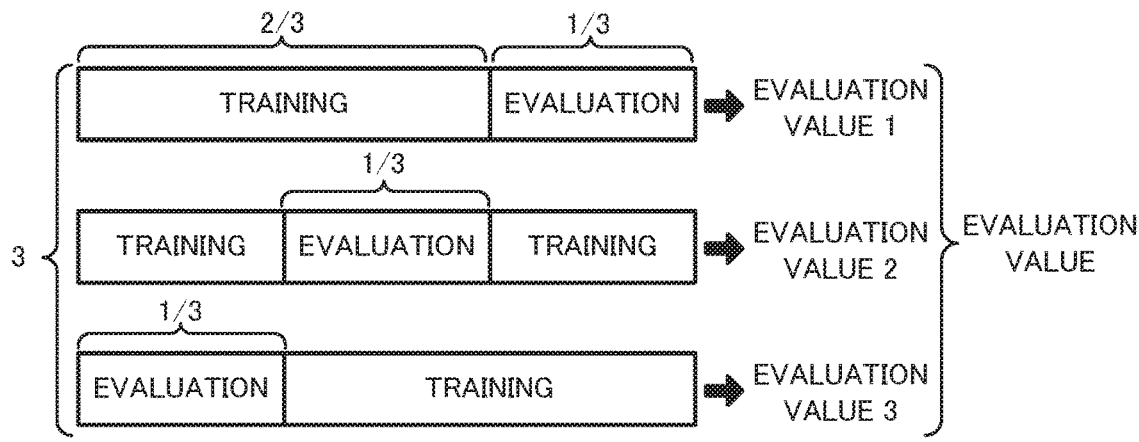

N EVALUATION DATA SETS AS WHICH 1/N OF TRAINING DATA SET IS USED ARE USED, AND EVALUATION VALUE OBTAINED FROM WHOLE TRAINING DATA SET IS ACQUIRED (N = 3 IN TOP DIAGRAM BELOW)

EVALUATION VALUE FOR EACH IDENTIFIER (AND COMBINATION OF IDENTIFIERS) IS ACQUIRED

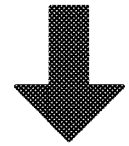

FIRST EVALUATION VALUE (EVALUATION VALUE OF IDENTIFIER A)

SECOND EVALUATION VALUE (EVALUATION VALUE OF IDENTIFIER B)

THIRD EVALUATION VALUE (EVALUATION VALUE OF IDENTIFIER A + IDENTIFIER B)

METHOD IN WHICH HIGHEST EVALUATION VALUE IS OBTAINED IS ADOPTED, AND TRAINING IS PERFORMED USING ALL ITEMS OF TRAINING DATA BY THIS METHOD (TRAINING OF BOTH IDENTIFIERS IS PERFORMED WHEN THIRD EVALUATION VALUE (EVALUATION VALUE OF IDENTIFIER A + IDENTIFIER B) IS HIGHEST AS ILLUSTRATED IN RIGHT DIAGRAM)

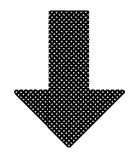

TRAINING OF IDENTIFIER A

TRAINING OF IDENTIFIER B

IDENTIFICATION APPARATUS, IDENTIFIER TRAINING METHOD, IDENTIFICATION METHOD, AND RECORDING MEDIUM

CROSS-REFERENCE TO RELATED APPLICATION

This application claims the benefit of Japanese Patent Application No. 2020-019275, filed on Feb. 7, 2020, the entire disclosure of which is incorporated by reference herein.

FIELD

The present disclosure relates to an identification apparatus, an identifier training method, an identification method, and a recording medium.

BACKGROUND

For example, a diagnostic apparatus disclosed in Unexamined Japanese Patent Application Kokai Publication No. 2017-45341 is conventionally known as an identification apparatus that identifies whether an image affected area is malignant or not. In the diagnostic apparatus, skin image data is subjected to image conversion such as site highlight, structure clarification, rotation, inversion, or the like to increase the amount of the image data, and the image data of which the amount has been increased is input into plural identifiers.

Identification precision is improved in comparison with conventional diagnostic apparatuses by integrating identification results from the plural identifiers to obtain a final identification result.

SUMMARY

According to an aspect of the present disclosure, an identification apparatus includes a processor and a memory configured to store a program to be executed by the processor. The processor is configured to acquire first image data obtained by capturing of an image of an affected area included in a skin or a mucosa by receiving first reception light. The first reception light is reflection light reflected from the affected area irradiated with first irradiation light including white light. The processor is further configured to acquire second image data obtained by capturing of an image of the affected area by receiving second reception light. The second reception light is light including light generated by fluorescent reaction in the affected area irradiated with second irradiation light. The second irradiation light includes light that allows the affected area to show fluorescent reaction when the affected area is irradiated with the light. The processor is further configured to identify the affected area based on the first image data and the second image data.

BRIEF DESCRIPTION OF THE DRAWINGS

A more complete understanding of this application can be obtained when the following detailed description is considered in conjunction with the following drawings, in which:

FIG. 14 is a diagram explaining cross validation in adoption identifier determination/training process according to Variation 3.

DETAILED DESCRIPTION

Figure 1:
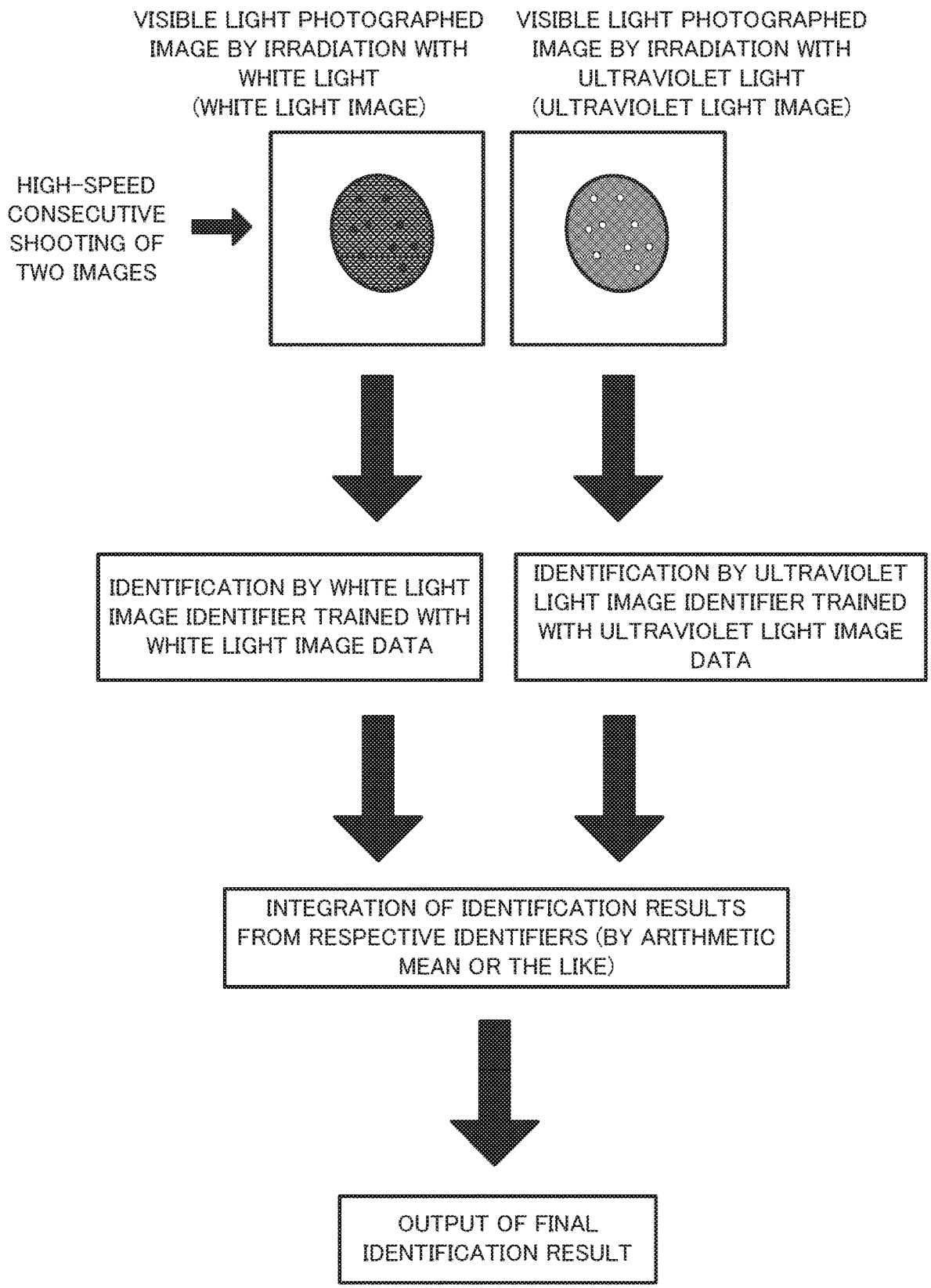
FIG. 1 is a diagram explaining the processing outline of an identification apparatus according to Embodiment 1.

An identification apparatus and the like according to embodiments of the present disclosure will be described below with reference to the drawings. In the drawings, the same or corresponding portions are denoted by the same reference characters.

Embodiment 1

An identification apparatus 100 according to Embodiment 1 of the present disclosure performs high-speed consecutive shooting with visible light for each of cases in which an affected area is first irradiated with white light (light in which visible light having each wavelength is uniformly mixed) as first irradiation light, and in which the affected area is irradiated with second irradiation light (for example, light having a wavelength of 320 nm to 440 nm, preferably 405 nm) allowing the affected area to show fluorescent reaction when the affected area is irradiated with the second irradiation light, as illustrated in FIG. 1. The identification apparatus 100 obtains, by the consecutive shooting, white light irradiation visible light photographed image data in the case of irradiation with white light (hereinafter referred to as "white light image data") and ultraviolet light irradiation visible light photographed image data in the case of irradiation with ultraviolet light (hereinafter referred to as "ultraviolet light image data"), and identifies the affected area captured in each of the white light image data and the ultraviolet light image data with an identifier trained for each of the white light image data and the ultraviolet light image data. The identification apparatus 100 obtains a final identification result on the basis of an identification result based on the white light image data and an identification result based on the ultraviolet light image data. In the present specification, claims, and abstract, "affected area" encompasses not only an area that has (that has been definitively diagnosed as having) a disease but also an area that may seem to have (that has not been definitively diagnosed as having) a disease. High-speed consecutive shooting refers to consecutive shooting at time intervals of not more than consecutive shooting reference time (for example, 1 second).

In the case of photographing by irradiation with white light, an early-stage keratotic plug is photographed to have a whitish color, and an advanced-stage keratotic plug is oxidized and photographed to have a blackish color, like melanin. However, irradiation with ultraviolet light allows a keratotic plug to show fluorescent reaction to generate light with yellow to red depending on the degree of progression of the keratotic plug. Accordingly, photographing with visible light by irradiation with ultraviolet light facilitates confirmation of the existence of a keratotic plug. A case in which many keratotic plugs exist in an affected area shows that the hair root is not damaged by malignant tumor, and the affected area is more likely to be benign. The identification apparatus 100 improves identification precision by obtaining a final identification result on the basis of an identification result based on white light image data and an identification result based on ultraviolet light image data using the above. The reason why high-speed consecutive shooting of an affected area is performed is because the positional deviation and time variation of images between the white light image data and the ultraviolet light image data are minimized.

As described above, irradiation with ultraviolet light allows a keratotic plug to show fluorescent reaction. More specifically, an increase in the number of keratotic plugs in an affected area (the increased possibility that the affected area is benign) results in an increase in an intensity of fluorescence having a porphyrin fluorescence wavelength (for example, a central fluorescence wavelength of 630 nm).

A spot producing fluorescent reaction by irradiation with ultraviolet light is not limited to a keratotic plug. For example, when a cell becomes a cancer or becomes in a variant state which is a precancerous state, the amount of autofluorescence substance is changed, and the intensity of fluorescence having a corresponding fluorescence wavelength is changed. Accordingly, photographing of the cell with a visible light camera enables detection of the increase and decrease of each intensity of fluorescence, and also enables improvement in identification precision in a case in which an affected area is malignant, for example, a cancer.

Specifically, when a cell becomes in a condition such as a cancer, intracellular oxygen is decreased due to, for example, damage to an epithelial cell, thereby increasing reduced nicotinamide adenine dinucleotide (NADH) and decreasing flavin adenine dinucleotide (FAD). Damage to the collagen of a stromal cell results in a decrease in the collagen and also in a decrease in porphyrin. The fluorescence wavelengths of such collagen, NADH, FAD, and porphyrin vary with changing an excitation wavelength. Basically, collagen, NADH, FAD, and porphyrin are in increasing order of central fluorescence wavelength. For example, when a central fluorescence wavelength in the case of irradiation with ultraviolet light as excitation light is taken as an example, the central fluorescence wavelengths of collagen, NADH, FAD, and porphyrin are 400 nm, 450 nm, 520 nm, and 630 nm, respectively.

Further, identification of an affected area using irradiation with ultraviolet light can be used not only for the skin but also for other sites. In particular, melanin existing in the skin absorbs ultraviolet rays. Therefore, less ultraviolet rays absorbed in a site with less melanin (for example, oral cavity, large intestine mucous membrane, uterine cervix, or the like) are achieved, and higher identification precision can be expected to be obtained by applying the present disclosure. Further, since lamina propria and lamina muscularis mucosae do not exist in the uterine cervix, a path to the stroma is shorter in the uterine cervix than those of the interiors of the oral cavity and the large intestine, and thus fluorescent reaction due to collagen is considered to be able to be detected with high sensitivity.

The present embodiment is described a case in which the skin is an affected area as an example of the affected area. Therefore, R-value, G-value, and B-value, or R-value and G-value are presumed to be used among 3-ch (channel) pixel values of RGB (red, green, blue) obtained by photographing an affected area irradiated with ultraviolet light by a visible light camera, in consideration of fluorescence (from yellow to red) for a keratotic plug. In contrast, in the case of an affected area (for example, mucosal) other than the skin, there is no keratotic plug, it is not necessary to take fluorescence from yellow to red into consideration, and therefore, only G-value and B-value may be used among the pixel values of RGB. However, even in a case in which an affected area without a keratotic plug is targeted, R-value, G-value, and B-value may be used because a component of R-value is not zero although being low.

Figure 2:
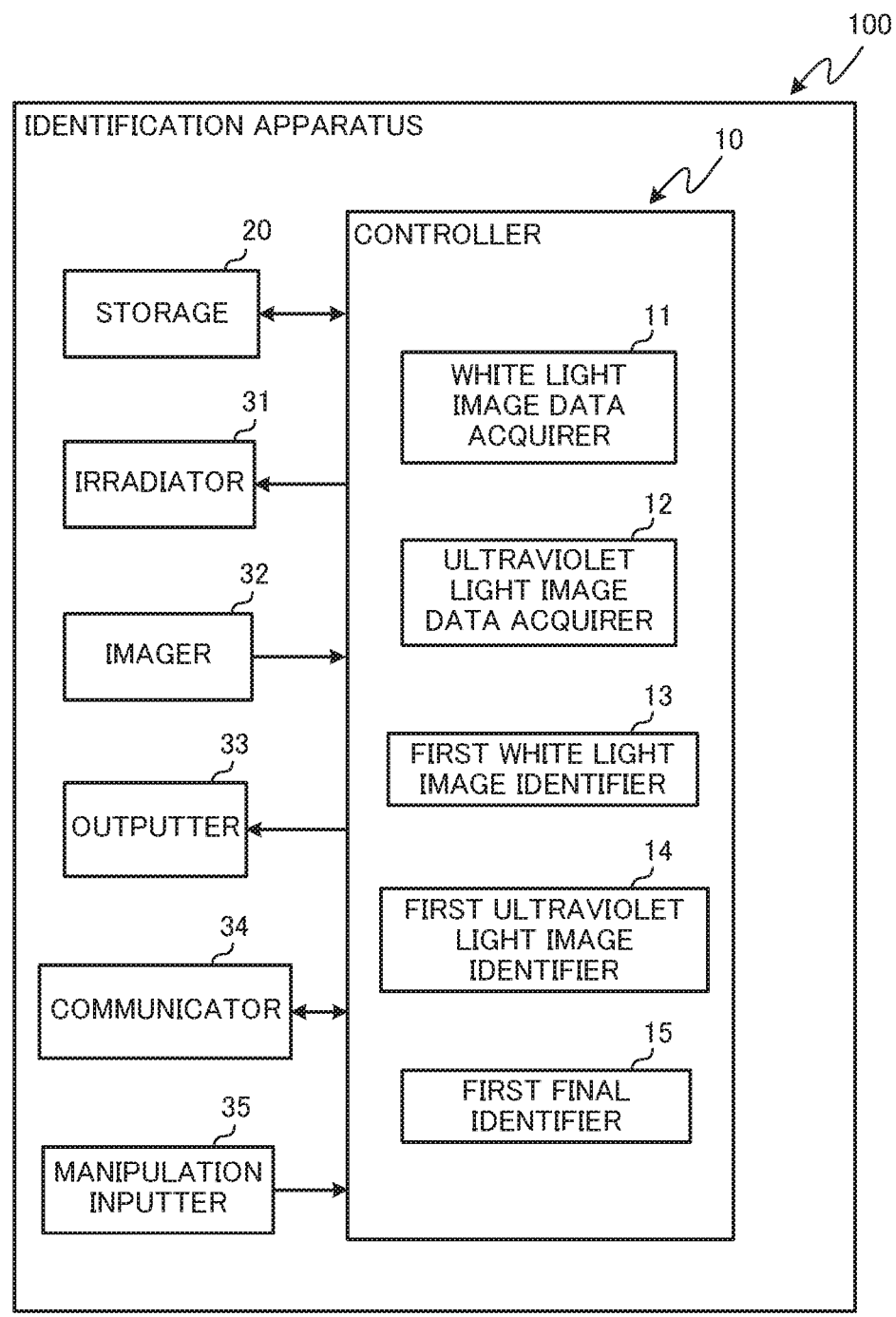
FIG. 2 is a diagram illustrating the functional configuration of an identification apparatus according to Embodiment 1.

The identification apparatus 100 according to Embodiment 1 includes a controller 10, a storage 20, an irradiator 31, an imager 32, an outputter 33, a communicator 34, and a manipulation inputter 35, as illustrated in FIG. 2.

The controller 10 includes a central processing unit (CPU) and the like, and implements the function of each unit (a white light image data acquirer 11, an ultraviolet light image data acquirer 12, a first white light image identifier 13, a first ultraviolet light image identifier 14, and a first final identifier 15) described later by executing a program stored in the storage 20.

The storage 20 includes a read only memory (ROM), a random access memory (RAM), and the like. A program executed by the CPU of the controller 10, and needed data are stored in the storage 20.

The irradiator 31 includes a device that emits white light as first irradiation light, such as a white light emitting diode (LED), and a device that emits ultraviolet light as second irradiation light, such as an ultraviolet light LED, and irradiates a site (such as the affected area of a patient), imaged by the imager 32, with white light or ultraviolet light. The controller 10 can instruct whether irradiation with white light or ultraviolet light is performed by the irradiator 31. The irradiator 31 may perform irradiation even with light including other light (for example, ultraviolet light) as the first irradiation light as long as the light includes white light. The irradiator 31 may perform irradiation with light including optional light (for example, infrared light) as the second irradiation light as long as the light includes light allowing an affected area to produce fluorescent reaction in the case of irradiating the affected area with the light. The light is not limited to ultraviolet light. In the present embodiment, ultraviolet light includes near-ultraviolet light.

The imager 32 includes an imaging element such as a complementary metal oxide semiconductor (CMOS) image sensor, and captures an image into image data for training or (unknown) image data to be identified. In the imager 32, a color filter is disposed in front of the image sensor in order to perform color separation of visible light to be received into the three primary colors of light, and another filter may be further disposed in front of the image sensor in order to appropriately receive fluorescence light. In order to appropriately represent fluorescence light, the imager 32 may apply a digital filter to image data obtained by capturing of an image. The controller 10 acquires the image data obtained by the capturing by the imager 32, as image data including a set of 3-ch pixel values of RGB.

In the present embodiment, a case in which the imager 32 receives visible light is described. However, the imager 32 may receive and image not only visible light but also light including optional light (for example, light including ultraviolet light or infrared light in addition to visible light (instead of visible light), or the like). In such a case, the kind of a filter may be changed (for example, a filter that extracts ultraviolet rays may be disposed) depending on received light.

It is not necessary to capture an image by the imager 32 when the controller 10 acquires image data. For example, when image data is stored in the storage 20, the controller 10 may acquire the image data by reading out the image data from the storage 20. The controller 10 may acquire image data from an external server or the like via the communicator 34. When image data is acquired from the storage 20, an external server, or the like in such a manner, the identification apparatus 100 need not include the irradiator 31 or the imager 32.

The outputter 33 is a device for outputting, for example, a result in which the controller 10 identifies an affected area captured in image data obtained by the capturing by the imager 32. For example, the outputter 33 is a liquid crystal display or an organic electro-luminescence (EL) display. In such a case, the outputter 33 functions as a display. However, the identification apparatus 100 may include such a display as the outputter 33, or may include the outputter 33 as an interface for connection of an external display instead of the display. The identification apparatus 100 displays an identification result or the like on the external display connected via the outputter 33 when including the outputter 33 as the interface. The identification apparatus 100 may include, as the outputter 33, a speaker or the like that provides as a sound output an identification result of the affected area or the like.

The communicator 34 is a device (a network interface or the like) for transmitting and receiving data to and from another external apparatus (for example, a server in which the database of image data is stored, or the like). The controller 10 can acquire image data and the like via the communicator 34.

The manipulation inputter 35, which is a device that accepts manipulated input into the identification apparatus 100 by a user, is, for example, a keyboard, a mouse, a touch panel, or the like. The identification apparatus 100 accepts an instruction or the like from a user via the manipulation inputter 35.

The functions of the controller 10 will now be described. The controller 10 implements the functions of the white light image data acquirer 11, the ultraviolet light image data acquirer 12, the first white light image identifier 13, the first ultraviolet light image identifier 14, and the first final identifier 15.

The white light image data acquirer 11 acquires white light image data obtained by receiving and imaging reflection light (first reception light) reflected from an affected area irradiated with white light (first irradiation light). The white light image data is image data including a set of 3-ch pixel values of RGB which are the color components of an RGB color space. According to each pixel, the white light image data includes R-value indicating the degree of the red of the pixel, G-value indicating the degree of the green of the pixel, and B-value indicating the degree of the blue of the pixel. The white light image data is also referred to as first image data.

The ultraviolet light image data acquirer 12 acquires ultraviolet light image data obtained by receiving and imaging light (second reception light) including light generated by fluorescent reaction in an affected area irradiated with ultraviolet light (second irradiation light). Like the white light image data, the ultraviolet light image data is image data including a set of 3-ch pixel values of RGB, and includes R-value, G-value, and B-value according to each pixel. The ultraviolet light image data is also referred to as second image data.

Both the first white light image identifier 13 and the first ultraviolet light image identifier 14 are identifiers for an image, based on a convolutional neural network (CNN) which is a kind of a deep neural network (DNN). The controller 10 functions as the first white light image identifier 13 as well as the first ultraviolet light image identifier 14 by executing a program that implements an identifier based on the CNN.

The first white light image identifier 13 includes an input layer into which white light image data acquired by the white light image data acquirer 11 is input, an output layer, and an intermediate layer between the input layer and the output layer, and outputs, from the output layer, the result of identifying an affected area captured in the white light image data. The first white light image identifier 13 is also referred to as a first identifier. Training a machine learning model based on a training data set to which a correct answer label indicating whether an affected area captured in each image data is benign or malignant is assigned allows the first white light image identifier 13 to output, from the output layer, a probability that the affected area is malignant, when white light image data with a captured image of the affected area is input into the first white light image identifier 13 (the training is performed so that a probability that the affected area is malignant is output in the present embodiment although the training can also be performed so that a probability that the affected area is benign is output from the output layer). Accordingly, the controller 10 executes a first identification process by the first white light image identifier 13.

The first ultraviolet light image identifier 14 includes an input layer into which ultraviolet light image data acquired by the ultraviolet light image data acquirer 12 is input, an output layer, and an intermediate layer between the input layer and the output layer, and outputs, from the output layer, the result of identifying an affected area captured in the ultraviolet light image data. The first ultraviolet light image identifier 14 is also referred to as a second identifier. Training a machine learning model based on a training data set to which a correct answer label indicating whether an affected area captured in each image data is benign or malignant is assigned allows the first ultraviolet light image identifier 14 to output, from the output layer, a probability that the affected area is malignant, when ultraviolet light image data with a captured image of the affected area is input into the first ultraviolet light image identifier 14 (the training is performed so that a probability that the affected area is malignant is output in the present embodiment although the training can also be performed so that a probability that the affected area is benign is output from the output layer). Accordingly, the controller 10 executes a second identification process by the first ultraviolet light image identifier 14.

The first final identifier 15 obtains a final identification result using both an output (probability that the affected area captured in the white light image data is malignant) from the first white light image identifier 13 and an output (probability that the affected area captured in the ultraviolet light image data is malignant) from the first ultraviolet light image identifier 14. Basically, the first final identifier 15 simply arithmetically averages the output from the first white light image identifier 13 and the output from the first ultraviolet light image identifier 14 to obtain the final identification result, without limitation thereto. The first final identifier 15 may multiply, by an appropriate weight, each of the output from the first white light image identifier 13 and the output from the first ultraviolet light image identifier 14, and calculate the weighted mean of both the outputs, to obtain the final identification result.

The functional configuration of the identification apparatus 100 has been described above. An identifier training process will now be described with reference to FIG. 3. The process is a process for allowing the first white light image identifier 13 and the first ultraviolet light image identifier 14 to learn training data based on white light image data or ultraviolet light image data by supervised learning. The process is executed in such learning. However, it is necessary to complete the execution before at least an identification process described below is executed.

First, the controller 10 executes a training data generation process to generate a training data set necessary for supervised learning of the CNNs of the first white light image identifier 13 and the first ultraviolet light image identifier 14 (step S101). The training data generation process is a process of generating a white light training data set for training the first white light image identifier 13 and an ultraviolet light training data set for training the first ultraviolet light image identifier 14. The details of the process will be described later. Such a training data set is a training data aggregate including image data to which a correct answer label is assigned. The correct answer label indicates whether an affected area captured in the image data to which the correct answer label is assigned is benign or malignant.

In the present embodiment, a CNN is intended to be trained so that input of image data with a captured image of an affected area results in output of the probability of the degree of the malignancy of the affected area, and therefore, "benign/malignant" as a correct answer label is assigned to the image data included in the training data set. In a case in which the training data sets have been already prepared, the process of step S101 can be omitted. In this case, subsequent processes are carried out using the white light training data set and ultraviolet light training data set that have been already prepared. The CNN can be trained to output what disease might be included in an affected area at a higher probability, giving a probability of each disease, rather than to output a probability that the affected area is malignant. In this case, image data to which the disease name of the affected area (for example, melanoma (malignant), basal cell cancer (malignant), nevus pigmentosus (benign), seborrheic keratosis (benign), or the like) is assigned as a correct answer label is used as training data.

Referring back to FIG. 3, the controller 10 then trains the CNN of the first white light image identifier 13 using the white light training data set generated in step S101 (step S102). Specifically, the controller 10 takes, from the white light training data set, one item of white light image data to which a correct answer label is assigned. A weighting factor in the CNN is updated by an error back propagation method so that a difference (error) becomes small between a value output from the output layer when the white light image data is input into the input layer of the CNN of the first white light image identifier 13 and the correct answer label assigned to the white light image data. The controller 10 repeats a process of taking another item of white light image data from the white light training data set and updating the weighting factor in the CNN by the error back propagation method again. The number of such repetitions is optional. However, the weighting factor in the CNN may be updated once according to each of all the items of the white light image data by, for example, the repetitions of which the number is the number of the items of the white light image data included in the white light training data set.

Then, the controller 10 trains the CNN of the first ultraviolet light image identifier 14 using the ultraviolet light training data set generated in step S101 (step S103), and ends the identifier training process. The specific process content of step S103 is similar to the process content of step S102 except that ultraviolet light image data is used instead of the white light image data. Step S102 and step S103 are also referred to as training steps.

Figure 4:
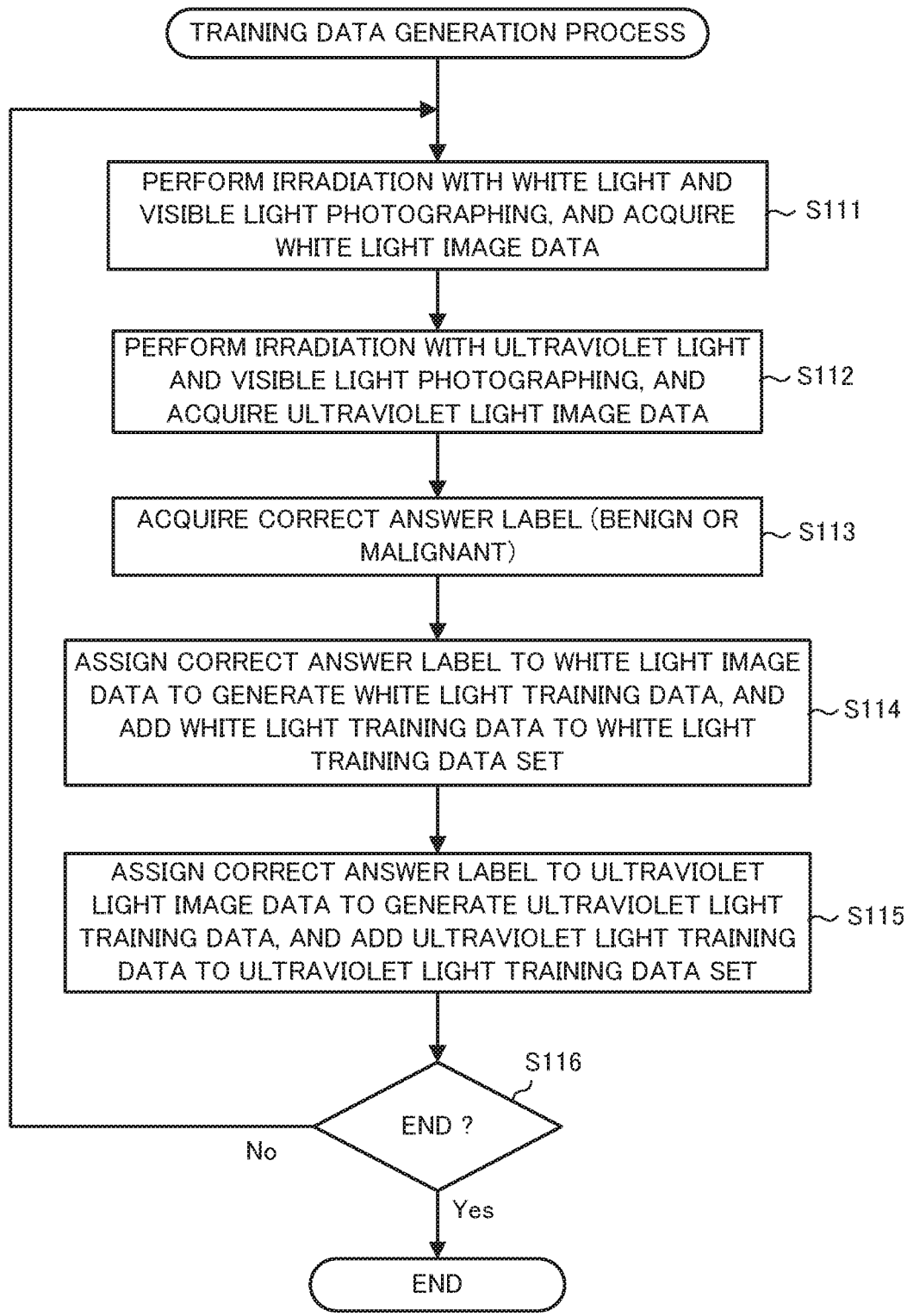
FIG. 4 is a flow chart of a training data generation process according to Embodiment 1.

The identifier training process has been described above. The training data generation process executed in the step S101 described above will now be described with reference to FIG. 4. It is necessary that an affected area known to be benign or malignant has been prepared (or the affected area is diagnosed as benign or malignant whenever the affected area is photographed) when the training data generation process is executed. However, the training data generation process may continue to be executed for a long period such as several months or several years. For example, the following processes of steps S111 to S115 may be executed whenever a doctor examines a new affected area for several months.

First, the imager 32 receives and images (performs visible-light photographing of) visible light reflected from an affected area in the state of irradiating the affected area with white light by the irradiator 31, and the white light image data acquirer 11 acquires white light image data (step S111).

Then, the imager 32 captures an image of the affected area by receiving visible light (including reflected light and generated fluorescence light) from the affected area in a state in which the affected area photographed in step S111 is irradiated with ultraviolet light by the irradiator 31, which is visible-light photographing, and the ultraviolet light image data acquirer 12 acquires ultraviolet light image data (step S112). For the visible-light photographing of step S111 and the visible-light photographing of step S112, it is desirable to perform high-speed consecutive shooting at a minimized interval; however, in Embodiment 1, the photographing is not limited to the high-speed consecutive shooting, but the photographing may be performed at an interval of 2 to 3 minutes, and the photographing may be performed at an interval of several days.

Then, the controller 10 acquires, from the manipulation inputter 35, the correct answer label of the affected area photographed in step S111 and step S112 (step S113). For example, a doctor diagnoses whether a photographed affected area is benign or malignant, and the diagnosis result (benign/malignant) is input via the manipulation inputter 35 to allow the controller 10 to acquire the diagnosis result. For example, time for which biopsy is performed (a lesion is removed) to obtain a pathological examination result or the diagnosis result is decided without biopsy by a consensus of several experts is often needed before the diagnosis result is obtained. Therefore, the execution of step S113 may require a time period of several days, several months, or several years. The acquired diagnosis result becomes a correct answer label assigned to the image data photographed in step S111 and step S112.

The controller 10 assigns the correct answer label acquired in step S113 to the white light image data acquired in step S111 to generate white light training data, and adds the white light training data to the white light training data set stored in the storage 20 (step S114). When the white light training data set has not yet been stored in the storage 20, a white light training data set consisting of one item of the white light training data generated in this case is stored in the storage 20.

Then, the controller 10 assigns the correct answer label acquired in step S113 to the ultraviolet light image data acquired in step S112 to generate ultraviolet light training data, and adds the ultraviolet light training data to the ultraviolet light training data set stored in the storage 20 (step S115). When the ultraviolet light training data set has not yet been stored in the storage 20, an ultraviolet light training data set consisting of one item of the ultraviolet light training data generated in this case is stored in the storage 20.

The controller 10 determines whether or not to end the training data generation process (step S116). The end is determined, for example, in a case in which a doctor inputs the instruction of ending the training data generation process from the manipulation inputter 35, such as the case of completely finishing the input of the photographing and diagnosis results of the affected area prepared in advance by a doctor. When the end is not determined (step S116; No), the process goes back to step S111.

Figure 3:
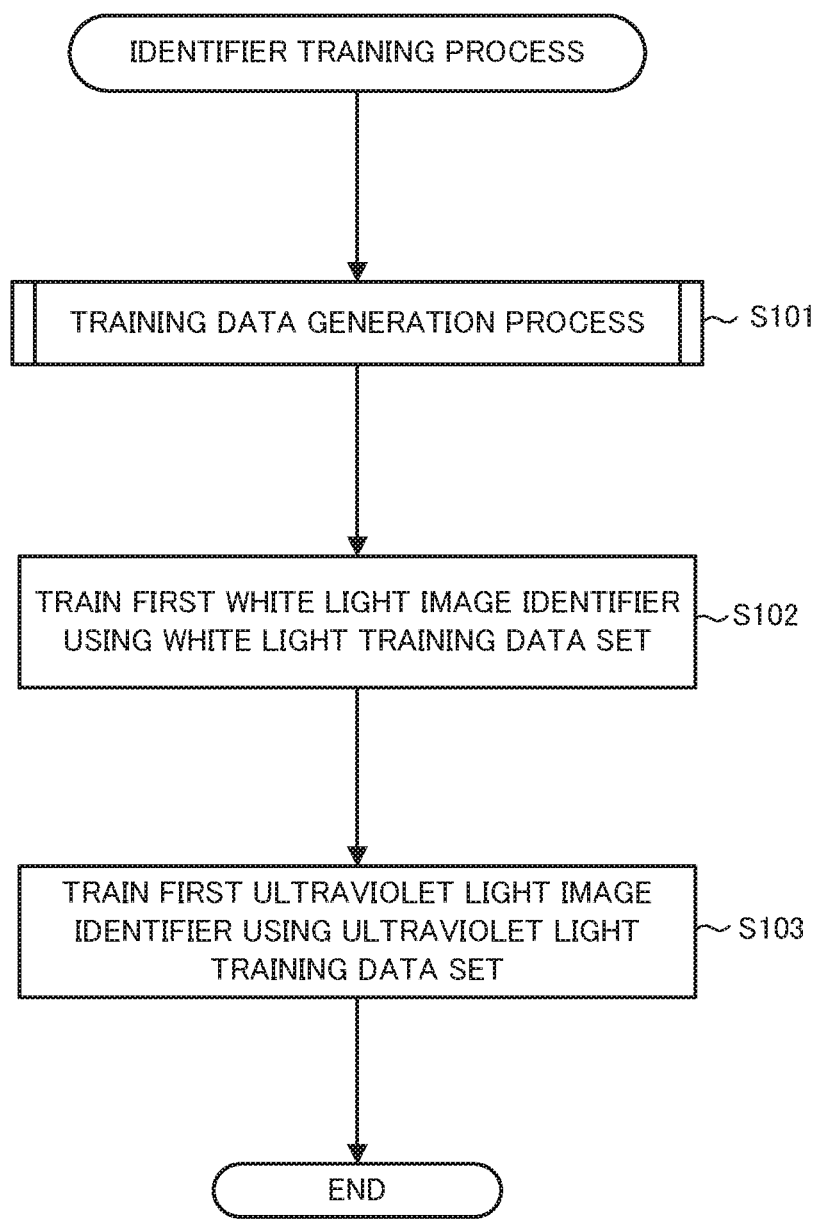
FIG. 3 is a flow chart of an identifier training process according to Embodiment 1.

When the end is determined (step S116; Yes), the training data generation process is ended to go back to the process from step S102 of the identifier training process (FIG. 3). Although the white light training data set and the ultraviolet light training data set are simultaneously generated in the training data generation process described above, it is also acceptable to generate only one training data set of both thereof. For example, when the white light training data set has already existed, it is also acceptable to skip the process for the white light image data, of the processes described above, and to generate only the ultraviolet light training data set.

As described above, a required time period between photographing of the image and definitive diagnosis (between step S112 and step S113), or a required interval between medical examinations (interval of step S111 repeated in loop) may be several months or more. Accordingly, it is also acceptable to store, in a database in advance, image data and a correct answer label acquired in processes similar to the steps S111 to S113 described above prior to the training data generation process, and to read out the image data and the correct answer label from the database to thereby perform the training data generation process.

Each CNN of the first white light image identifier 13 and the first ultraviolet light image identifier 14 is trained in the training data generation process and identifier training process described above. An identification process of identifying (inferring) the benignity and malignancy of an (unknown) affected area to be identified using the first white light image identifier 13 and the first ultraviolet light image identifier 14 in which training is performed in such a manner will now be described with reference to FIG. 5.

First, the irradiator 31 irradiates an affected area to be identified with white light, and the white light image data acquirer 11 acquires, as white light image data, the R-, G-, and B-values of an image obtained by capturing of an image of the affected area by the imager 32 by irradiating by the irradiator 31 the affected arear to be identified with the white light and receiving visible light reflected from the affected area irradiated with the white light (step S201). Step S201 is also referred to as a first image data acquisition step.

Then, the ultraviolet light image data acquirer 12 acquires, as ultraviolet light image data, the R-, G-, and B-values of an image obtained by capturing of an image of an affected area by the imager 32 by receiving visible light (including reflected light and generated fluorescence light) from the affected area irradiated with ultraviolet light in a state in which the affected area to be identified is irradiated with the ultraviolet light by the irradiator 31 (step S202). Step S202 is also referred to as a second image data acquisition step. For the visible-light photographing of step S201 and the visible-light photographing of step S202, it is desirable to perform high-speed consecutive shooting at a minimized interval; however, in Embodiment 1, the photographing is not limited to the high-speed consecutive shooting, but the photographing may be performed at an interval of 2 to 3 minutes, and the photographing may be performed at an interval of several days or several months.

The controller 10 inputs, into the first white light image identifier 13, the white light image data acquired in step S201, and acquires an identification result obtained by the first white light image identifier 13 (the output value of the CNN of the first white light image identifier 13) (step S203).

Then, the controller 10 inputs, into the first ultraviolet light image identifier 14, the ultraviolet light image data acquired in step S202, and acquires an identification result obtained by the first ultraviolet light image identifier 14 (the output value of the CNN of the first ultraviolet light image identifier 14) (step S204).

The first final identifier 15 computes the arithmetic mean of the output value of the CNN of the first white light image identifier 13, acquired in step S203, and the output value of the CNN of the first ultraviolet light image identifier 14, acquired in step S204, (sum of both values/2), and determines the computed arithmetic mean as an identification result which is final (final identification result) (step S205). Step S205 is also referred to as a final identification step.

The controller 10 displays the final identification result on the outputter 33 (step S206), and ends the identification process. In such a manner, the controller 10 identifies the affected area according to the CNN which is a model in which machine learning is performed. The present embodiment is described using a CNN as an example of the learning model used in identification of an affected area. In the identification apparatus 100, however, a support vector machine (SVM), logistic regression, random forest, Adaboost, Gradient boosting, a recurrent neural network (RNN), or the like may be used, or two or more thereof may be used in combination.

In the identification process described above, an identification result based on usual white light image data and an identification result based on ultraviolet light image data can be integrated to obtain a final identification result. In the case of using only the white light image data, it may be difficult to make identification, for example, between a keratotic plug and melanin. However, use of the ultraviolet light image data facilitates the identification between a keratotic plug and melanin. As described above, an affected area with many keratotic plugs is highly likely to be benign. Accordingly, use of the final identification result determined as described above can result in improvement in identification performance in comparison with conventional identification (based on only white light image data).

The ultraviolet light image data acquirer 12 described above acquires, as ultraviolet light image data, the R-, G-, and B-values of the image obtained by capturing of the image of the affected area by the imager 32 by receiving visible light (including reflected light and generated fluorescence light) from the affected area irradiated with ultraviolet light in the state in which the affected area to be identified is irradiated with ultraviolet light by the irradiator 31. However, since the pixel values important in the identification of a keratotic plug are R-value and G-value, use of no B-value can also be considered to have less influence on identification performance. Thus, the ultraviolet light image data acquirer 12 may acquire, as ultraviolet light image data, the R- and G-values of an image obtained by imaging by the imager 32 as described above.

In such a case, the input layer of the CNN of the first ultraviolet light image identifier 14 is configured so that ultraviolet light image data including R-value and G-value (including no B-value) is input into the input layer. In the case of the identifier training process, the controller 10 trains the first ultraviolet light image identifier 14 using an ultraviolet light image training data set generated using the ultraviolet light image data including R-value and G-value by machine learning. In such a manner, the first final identifier 15 can integrate the result of identifying the affected area using the white light image data including 3-ch RGB by the first white light image identifier 13 and the result of identifying the affected area using the ultraviolet light image data including 2-ch RG by the first ultraviolet light image identifier 14, to determine the final identification result.

In such a case, the ultraviolet light image data includes only 2-ch RG, and therefore, a data amount can be reduced in comparison with the case of using 3-ch RGB. As described above, use of the 2-ch RG of the ultraviolet light image data is considered to enable the existence or nonexistence of a keratotic plug to determined, and therefore, in such a case, identification performance can also be improved in comparison with conventional identification (based on only white light image data).

In Embodiment 1, the white light training data set and the ultraviolet light training data set are independent of each other. Therefore, for example, for the white light training data set, use of published training data enables the process for the white light image data, of the training data generation processes described above, to be skipped to shorten time required for the training data generation processes. In addition, it is not necessary to introduce a facility for high-speed consecutive shooting because it is not necessary to perform high-speed consecutive shooting for white light image data and ultraviolet light image data even when an affected area is identified.

Variation 1

In Embodiment 1 as described above, white light image data and ultraviolet light image data are input into the separate identifiers, respectively, to identify the affected area. However, it is also conceivable that white light image data and ultraviolet light image data are collectively input into one identifier. Such Variation 1 will be described.

Figure 6:
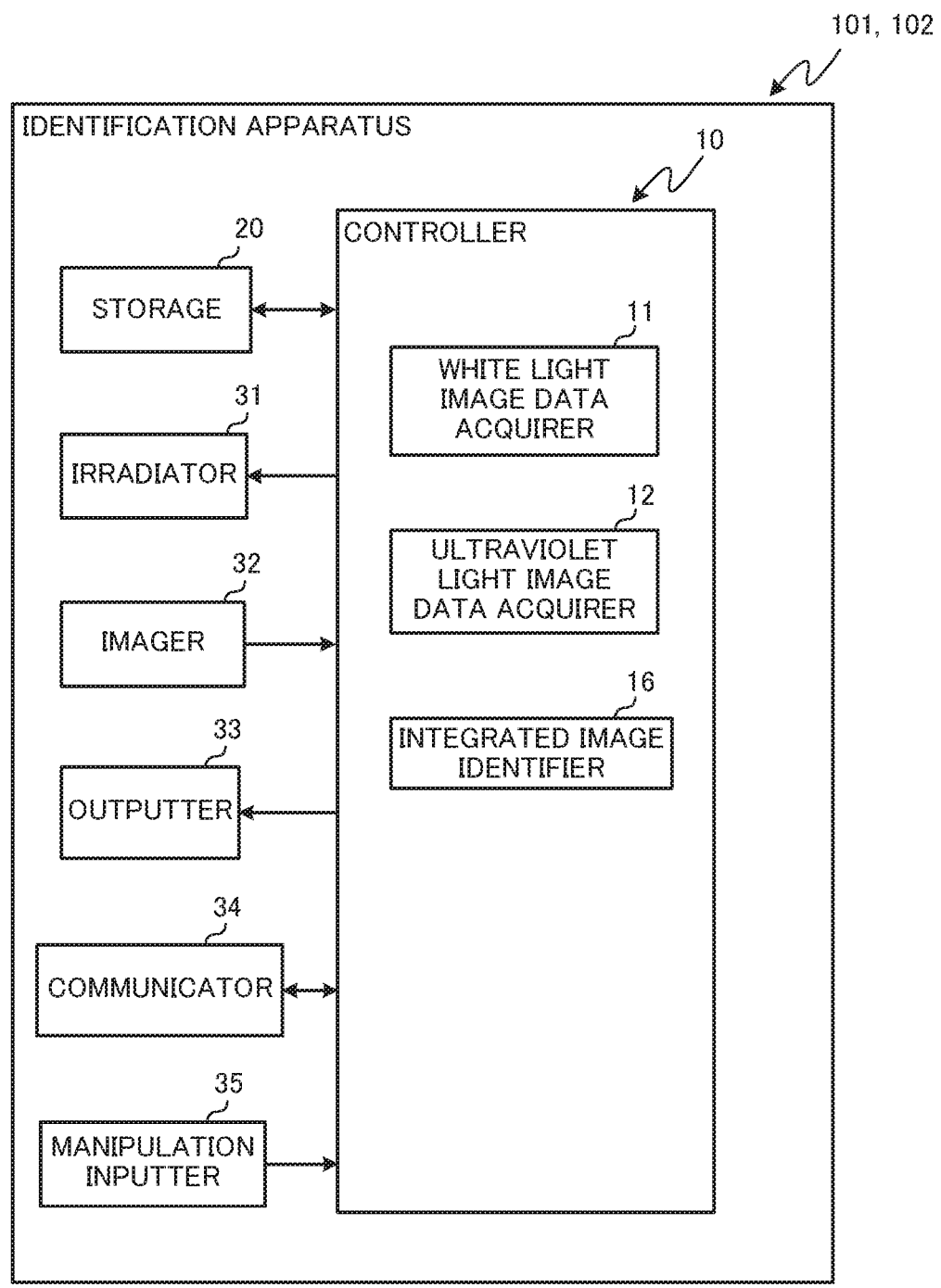
FIG. 6 is a diagram illustrating the functional configuration of an identification apparatus according to Variation 1.

The functional configuration of an identification apparatus 101 according to Variation 1 is a configuration in which the first white light image identifier 13, first ultraviolet light image identifier 14, and first final identifier 15 of the identification apparatus 100 according to Embodiment 1 are replaced with an integrated image identifier 16, as illustrated in FIG. 6.

The integrated image identifier 16 is also an identifier using, as input data, image data based on CNN which is a kind of DNN, like the first white light image identifier 13 and the first ultraviolet light image identifier 14. A controller 10 functions as the integrated image identifier 16 by executing a program that implements the identifier based on the CNN. However, each of the first white light image identifier 13 and the first ultraviolet light image identifier 14 accepts one item of image data as input data, whereas the integrated image identifier 16 accepts, as input data, one item of integrated image data into which two items of image data are unified.

In other words, the integrated image identifier 16 includes an input layer into which integrated image data including 6-ch RGB into which white light image data of 3-ch RGB acquired by a white light image data acquirer 11 and ultraviolet light image data of 3-ch RGB acquired by an ultraviolet light image data acquirer 12 are unified is input, an output layer, and an intermediate layer between the input layer and the output layer. The integrated image identifier 16 outputs, from the output layer, the result of identifying an affected area captured in the white light image data and the ultraviolet light image data included in the integrated image data (6-ch).

The other configuration of the identification apparatus 101 is similar to the configuration of the identification apparatus 100, and therefore, the descriptions thereof are omitted. An integrated image learning process in which the integrated image identifier 16 is trained by supervised machine learning will now be described with reference to FIG. 7. The process is executed when the integrated image identifier 16 is trained. It is necessary to complete the execution at least prior to execution of an integrated image identification process described below.

First, the controller 10 executes an integrated training data generation process to generate an integrated training data set necessary for supervised machine learning of the CNN of the integrated image identifier 16 (step S301). The details of the integrated training data generation process will be described later. The integrated training data set is an aggregate of integrated image data to which correct answer labels are assigned. The integrated image data in Variation 1 is one item of image data including 6-ch RGB, into which white light image data of 3-ch RGB and ultraviolet light image data of 3-ch RGB, subjected to high-speed consecutive shooting, are unified.

Then, the controller 10 trains the CNN of the integrated image identifier 16 by machine learning using the integrated training data set generated in step S301 (step S302). Specifically, the controller 10 takes, from the integrated training data set, one item of integrated image data to which a correct answer label is assigned. A weighting factor in the CNN is updated by an error back propagation method so that a difference (error) becomes small between a value output from the output layer when the integrated image data is input into the input layer of the CNN of the integrated image identifier 16 and the correct answer label assigned to the integrated image data. The controller 10 repeats a process of taking another item of integrated image data from the integrated training data set and updating the weighting factor in the CNN is by the error back propagation method again. The number of such repetitions is optional. However, the weighting factor in the CNN may be updated once according to each of all the items of the integrated image data by, for example, the repetitions of which the number is the number of the items of the integrated image data included in the integrated training data set.

When the CNN of the integrated image identifier 16 is trained in step S302, the integrated image learning process is ended. The integrated training data generation process executed in step S301 described above will now be described with reference to FIG. 8. Like the training data generation process described above, it is necessary that an affected area known to be benign or malignant has been prepared (or the affected area is diagnosed as benign or malignant whenever the affected area is photographed) when the integrated training data generation process is executed. Like the training data generation process, however, the integrated training data generation process may continue to be executed for a long period such as several months or several years. For example, the following processes of steps S311 to S314 may be executed whenever a doctor examines a new affected area for several months.

Each process of from steps S311 to step S313 of the integrated training data generation process is similar to each process of from step S111 to step S113 of the training data generation process (FIG. 4) according to Embodiment 1, and therefore, the descriptions thereof are omitted. However, the visible light photographing of step S311 and the visible light photographing of step S312 are performed at a time interval of not more than consecutive shooting reference time by high-speed consecutive shooting. In other words, a time difference between the image capturing timing for the white light image data acquired in step S311 and the image capturing timing for the ultraviolet light image data acquired in step S312 is not more than the consecutive shooting reference time.

The controller 10 assigns the correct answer label acquired in step S313 to one item of integrated image data (6-ch RGB) into which the white light image data (3-ch RGB) acquired in step S311 and the ultraviolet light image data (3-ch RGB) acquired in step S312 are integrated and unified to generate integrated training data, and adds the integrated training data to the integrated training data set stored in a storage 20 (step S314). When the integrated training data set has not yet been stored in the storage 20, an integrated training data set consisting of one item of the integrated training data generated in this case is stored in the storage 20.

Then, the controller 10 determines whether or not to end the integrated training data generation process (step S315). The end is determined, for example, in a case in which a doctor inputs the instruction of ending the integrated training data generation process from the manipulation inputter 35, such as the case of completely finishing the input of the photographing and diagnosis results of the affected area prepared in advance by a doctor. When the end is not determined (step S315; No), the process goes back to step S311.

Figure 7:
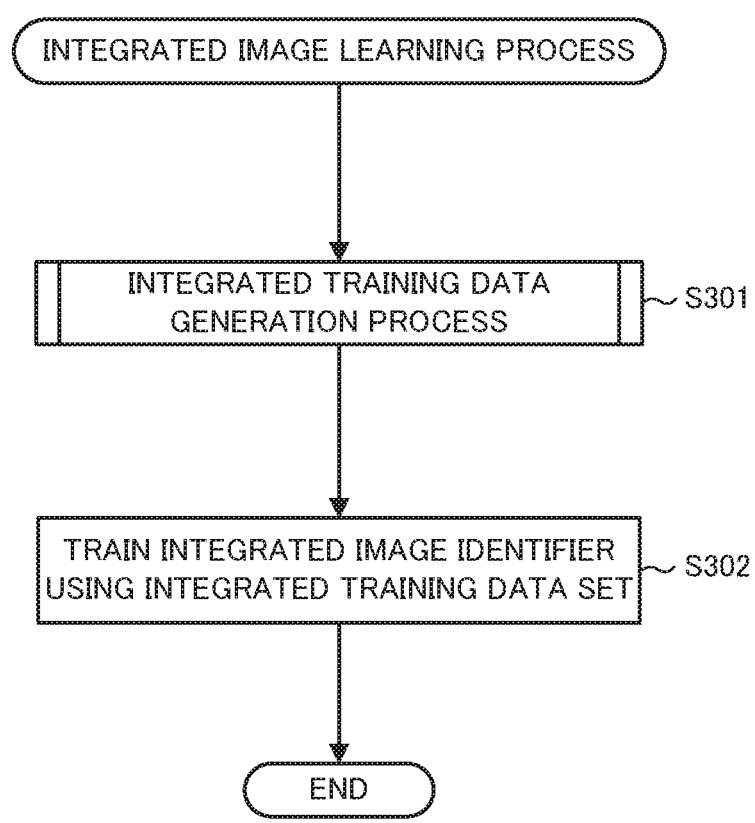
FIG. 7 is a flow chart of an integrated image learning process according to Variation 1.

When the end is determined (step S315; Yes), the training data generation process is ended to go back to the process from step S302 of the integrated image learning process (FIG. 7).

Figure 9:
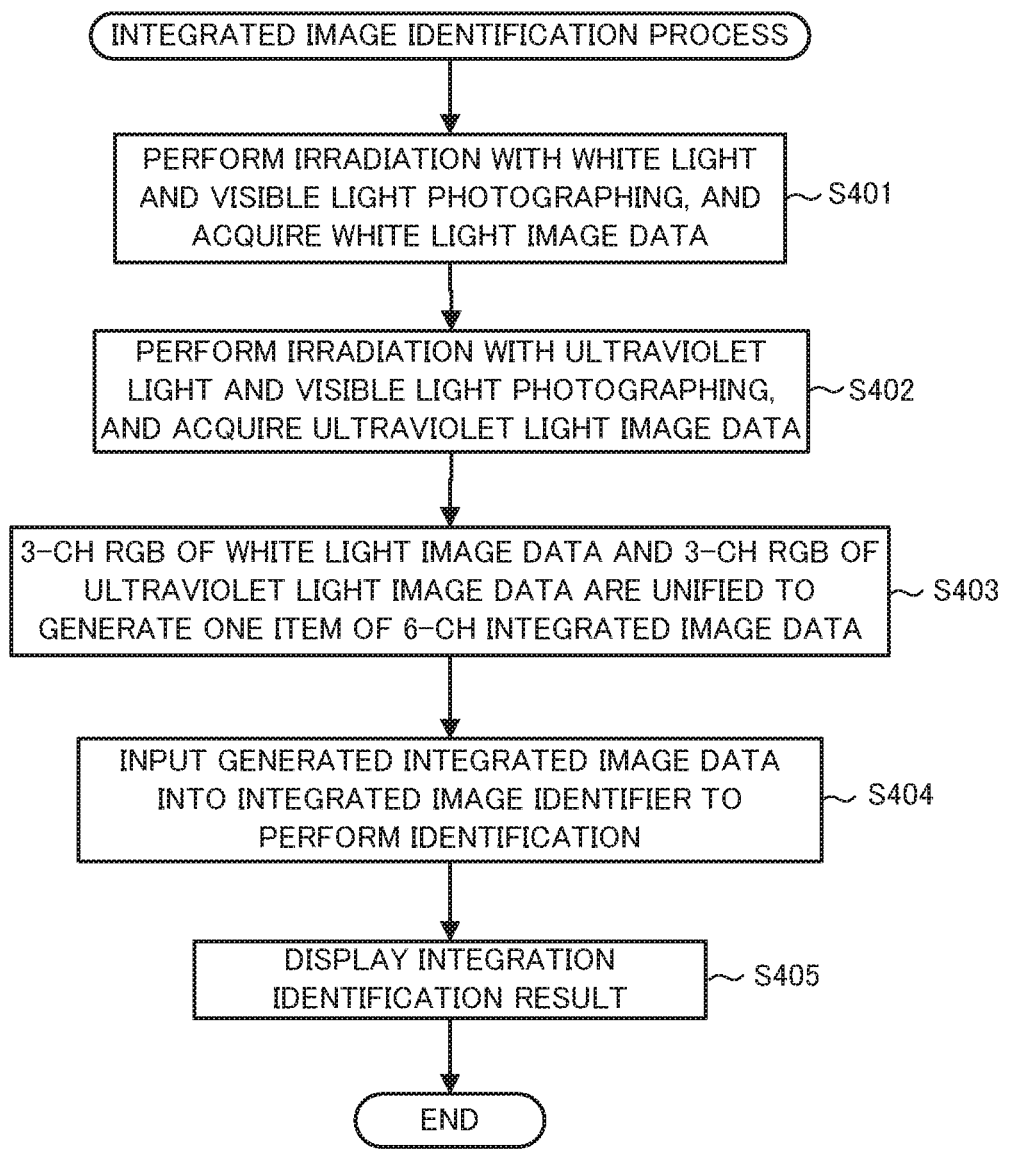
FIG. 9 is a flow chart of an integrated image identification process according to Variation 1.

The CNN of the integrated image identifier 16 is trained in the integrated training data generation process and the integrated image learning process described above. An integrated image identification process of identifying (inferring) the benignity and malignancy of the (unknown) affected area to be identified using the integrated image identifier 16 in which training is performed in such a manner will now be described with reference to FIG. 9.

Each process of step S401 and step S402 of the integrated image identification process is similar to each process of step S201 and step S202 of the identification process (FIG. 5) according to Embodiment 1, and therefore, the descriptions thereof are omitted. However, the visible light photographing of step S401 and the visible light photographing of step S402 are performed at a time interval of not more than consecutive shooting reference time by high-speed consecutive shooting. In other words, a time difference between the image capturing timing for the white light image data acquired in step S401 and the image capturing timing for the ultraviolet light image data acquired in step S402 is not more than the consecutive shooting reference time.

The controller 10 unifies the white light image data (3-ch RGB) acquired in step S401 and ultraviolet light image data (3-ch RGB) acquired in step S402 to generate one item of integrated image data (6-ch RGB) (step S403). The controller 10 inputs the generated integrated image data into the integrated image identifier 16, and acquires an identification result based on the integrated image identifier 16 (step S404).

The controller 10 displays the identification result based on the integrated image identifier 16 on an outputter 33 (step S405), and ends the integrated image identification process.

In the integrated image identification process described above, the identification can be performed using the integrated image data including both the usual information of white light image data and the information of ultraviolet light image data in which a keratotic plug can be easily determined, and therefore, identification performance can be improved in comparison with conventional identification (based on only white light image data). The positional deviation between the images of the white light image data and the ultraviolet light image data can be minimized by allowing a time difference between the image capturing timing for the white light image data and the image capturing timing for the ultraviolet light image data to be not more than consecutive shooting reference time. An identifier used in the identification is only the one integrated image identifier 16, and therefore, the identification process can be simplified.

Variation 2

In ultraviolet light image data, a component important for determining a keratotic plug is 2-ch RG. Thus, it is also conceivable that white image data (3ch RGB) and 2-ch RG of ultraviolet light image data are unified and input into one identifier. Such Variation 2 will be described.

The functional configuration of an identification apparatus 102 according to Variation 2 is a configuration in which the first white light image identifier 13, first ultraviolet light image identifier 14, and first final identifier 15 of the identification apparatus 100 according to Embodiment 1 are replaced with an integrated image identifier 16, as illustrated in FIG. 6. The configuration is similar to the configuration of the identification apparatus 101 according to Variation 1. However, the configurations differ from each other in a point in which the integrated image data accepted as input image data by the integrated image identifier 16 of the identification apparatus 101 is image data corresponding to 6-ch RGB whereas the integrated image data accepted as input image data by the integrated image identifier 16 of the identification apparatus 102 is image data corresponding to 5-ch in which the ch of blue (B) is removed from ultraviolet light image data. The integrated image data in Variation 2 is one item of image data including 5-ch, into which the 3-ch RGB of the white light image data and the 2-ch RG of the ultraviolet light image data, obtained by high-speed consecutive shooting, are unified.

In other words, in Variation 2, the integrated image identifier 16 includes an input layer into which the integrated image data including 5-ch, into which the 3-ch RGB of the white light image data acquired by a white light image data acquirer 11 and the 2-ch RG of ultraviolet light image data acquired by an ultraviolet light image data acquirer 12 are unified, is input, an output layer, and an intermediate layer between the input layer and the output layer, and outputs, from the output layer, the result of identifying an affected area captured in the white light image data and the ultraviolet light image data included in the integrated image data (5-ch).

Figure 10:
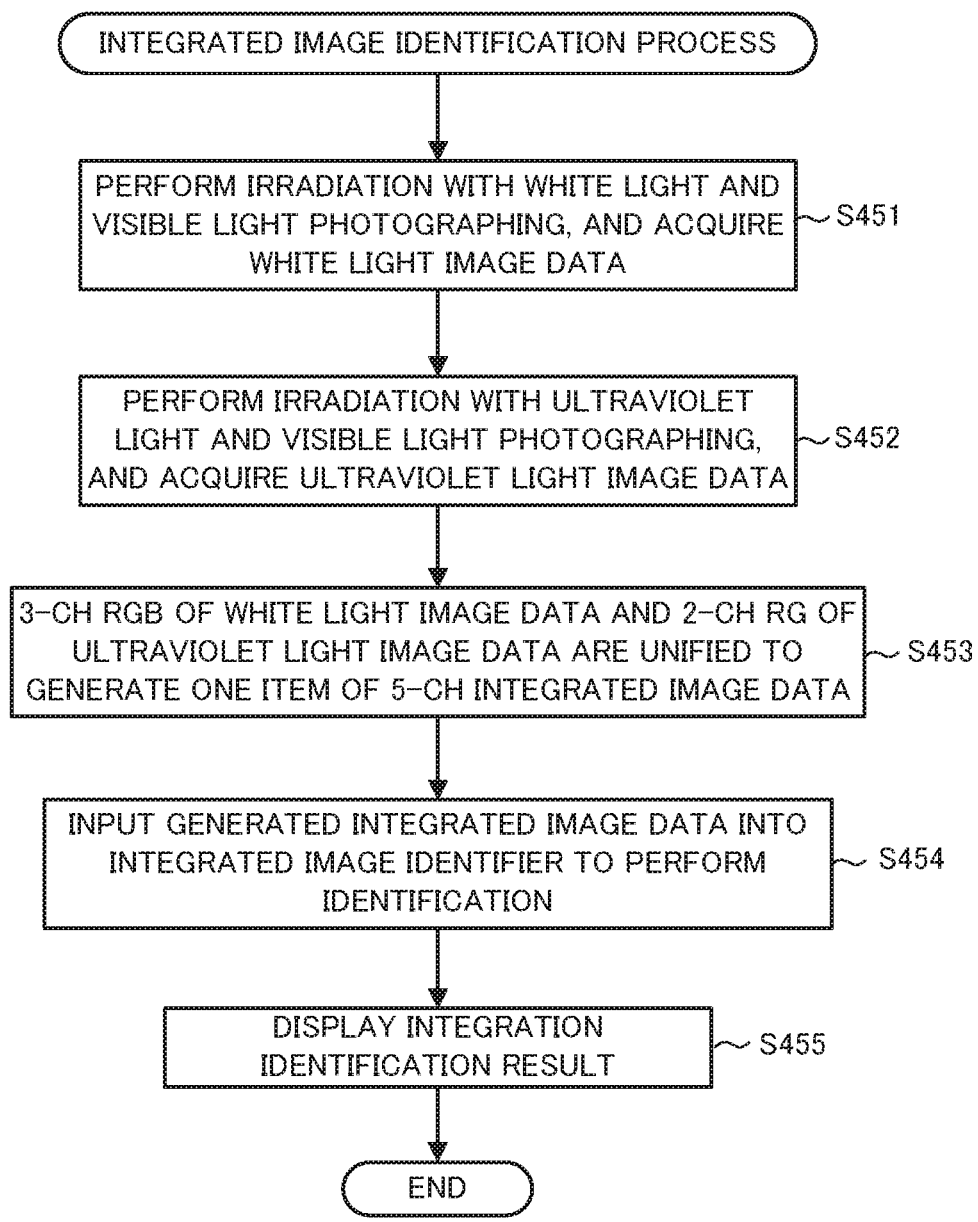
FIG. 10 is a flow chart of an integrated image identification process according to Variation 2.

The other configuration of the identification apparatus 102 is similar to the configuration of the identification apparatus 101, and therefore, the descriptions thereof are omitted. An integrated image learning process of training the integrated image identifier 16 and an integrated training data generation process are also similar to the integrated image learning process (FIG. 7) and integrated training data generation process (FIG. 8) according to Variation 1 except that the integrated image data is data corresponding to 5-ch rather than data corresponding to 6-ch, and the descriptions thereof are omitted. An integrated image identification process of identifying (inferring) the benignity and malignancy of an (unknown) affected area to be identified in Variation 2 will be described with reference to FIG. 10.

The processes of from step S451 to step S452 of the integrated image identification process according to Variation 2 are similar to the processes of from step S401 to step S402 of the integrated image identification process (FIG. 9) according to Variation 1, and therefore, the descriptions thereof are omitted. However, the ultraviolet light image data acquirer 12 acquires ultraviolet light image data including R-value and G-value (including no B-value) in step S452.

The controller 10 unifies white light image data (3-ch RGB) acquired in step S451 and ultraviolet light image data (2-ch RG) acquired in step S452 into one item of 5-ch integrated image data (step S453). The controller 10 inputs the generated integrated image data into the integrated image identifier 16, and acquires an identification result based on the integrated image identifier 16 (step S454).

The controller 10 displays the identification result based on the integrated image identifier 16 on an outputter 33 (step S455), and ends the integrated image identification process.

In the integrated image identification process according to Variation 2 described above, the identification can be performed using the integrated image data including both the usual information of white light image data and the information of ultraviolet light image data in which a keratotic plug can be easily determined, and therefore, identification performance can be improved in comparison with conventional identification (based on only white light image data). In addition, in the integrated image identification process according to Variation 2, the ultraviolet light image data is the 2-ch data of only R-value and G-value, and therefore, the load of the process can be reduced, and a data amount required for training can also be reduced, in comparison with the integrated image process according to Variation 1.

Variation 3

It has been described above that use of ultraviolet light image data enables the existence or non-existence of a keratotic plug to be relatively easily determined. With the utilization of the above, it is also conceivable to classify training data into training data using a keratotic plug and training data using no keratotic plug described below, and to train each of an identifier using a keratotic plug and an identifier using no keratotic plug using the classified training data. Such Variation 3 will be described below.

Figure 11:
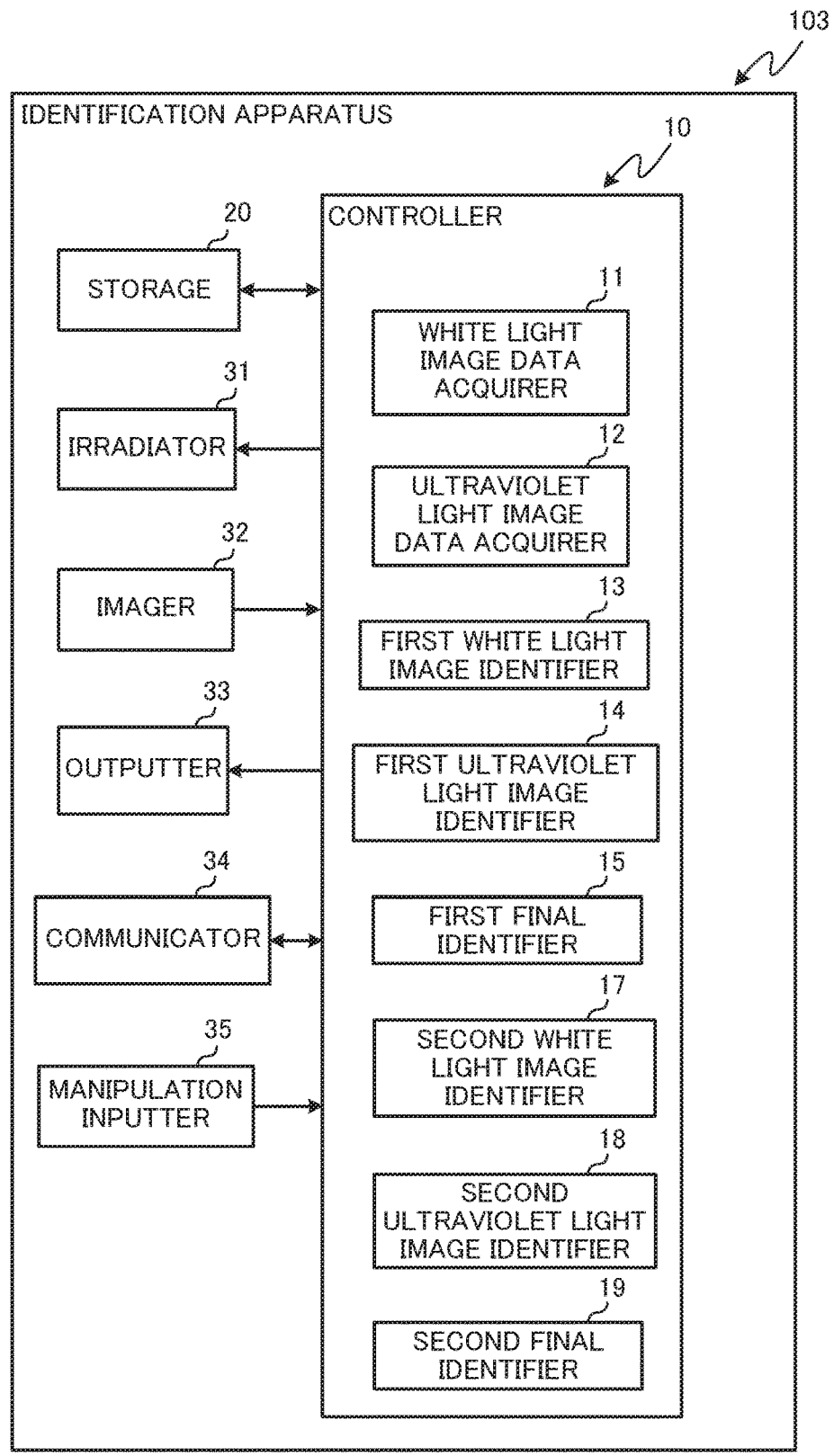
FIG. 11 is a diagram illustrating the functional configuration of an identification apparatus according to Variation 3.

The functional configuration of an identification apparatus 103 according to Variation 3 is a configuration in which a second white light image identifier 17, a second ultraviolet light image identifier 18, and a second final identifier 19 are added to the identification apparatus 100 according to Embodiment 1, as illustrated in FIG. 11.

Like the first white light image identifier 13, the second white light image identifier 17 is an identifier that identifies an affected area captured in white light image data. However, the first white light image identifier 13 according to Variation 3 is the identifier in which the affected area captured in the item of image data including the keratotic plug (image data with keratotic plug) among items of image data is targeted for identification. The second white light image identifier 17 is an identifier targeted for identification of an affected area captured in an item of image data in which no keratotic plug can be confirmed (image data in which it is impossible to confirm the existence of a keratotic plug because no keratotic plug exists so as to make fluorescence, although some keratotic plugs may exist; hereinafter, the image data is referred to as "image data without keratotic plug" for convenience although it cannot be said that any keratotic plug is completely absent) among the items of the image data.

Like the first ultraviolet light image identifier 14, the second ultraviolet light image identifier 18 is an identifier that identifies an affected area captured in ultraviolet light image data. However, the first ultraviolet light image identifier 14 according to Variation 3 is the identifier targeted for identification of the affected area captured in the item of image data with the keratotic plug (also referred to as "second image data with keratotic plug") among items of ultraviolet light image data, and the second ultraviolet light image identifier 18 is an identifier targeted for identification of an affected area captured in an item of image data without a keratotic plug (also referred to as "second image data without keratotic plug") among items of ultraviolet light image data. In the non-existence of a keratotic plug (or in the existence of a low level of keratotic plug), fluorescence is not generated due to a keratotic plug, but fluorescence with another color (for example, blue to green, or the like) is generated in the existence of, for example, cancer or the like, as described above. Accordingly, the second ultraviolet light image identifier 18 can identify the affected area using fluorescence other than fluorescence based on a keratotic plug.

A first final identifier 15 according to Variation 3 uses both of an output (the result of identifying the affected area captured in white light image data including the keratotic plug) from the first white light image identifier 13 and the output (the result of identifying the affected area captured in ultraviolet light image data including the keratotic plug) from the first ultraviolet light image identifier 14 to perform an adoption identifier determination/training process described below, and uses an adoption identifier allowed to perform determination and training by the process to obtain a final identification result. The second final identifier 19 uses both of an output (the result of identifying the affected area captured in white light image data including no keratotic plug) from the second white light image identifier 17 and an output (the result of identifying the affected area captured in ultraviolet light image data including no keratotic plug) from the second ultraviolet light image identifier 18 to perform the adoption identifier determination/training process described below, and uses the adoption identifier allowed to perform determination and training by the process to obtain the final identification result.

The other configuration of the identification apparatus 103 is similar to the configuration of the identification apparatus 100, and the descriptions thereof are omitted. An image learning process for the existence or non-existence of a keratotic plug which is a learning process in the identification apparatus 103 will now be described with reference to FIG. 12. The process is executed when the first white light image identifier 13, the first ultraviolet light image identifier 14, the second white light image identifier 17, and the second ultraviolet light image identifier 18 are trained by supervised machine learning. It is necessary to complete the execution at least prior to execution of an identification process for use of the existence or non-existence of a keratotic plug described below.

Figure 8:
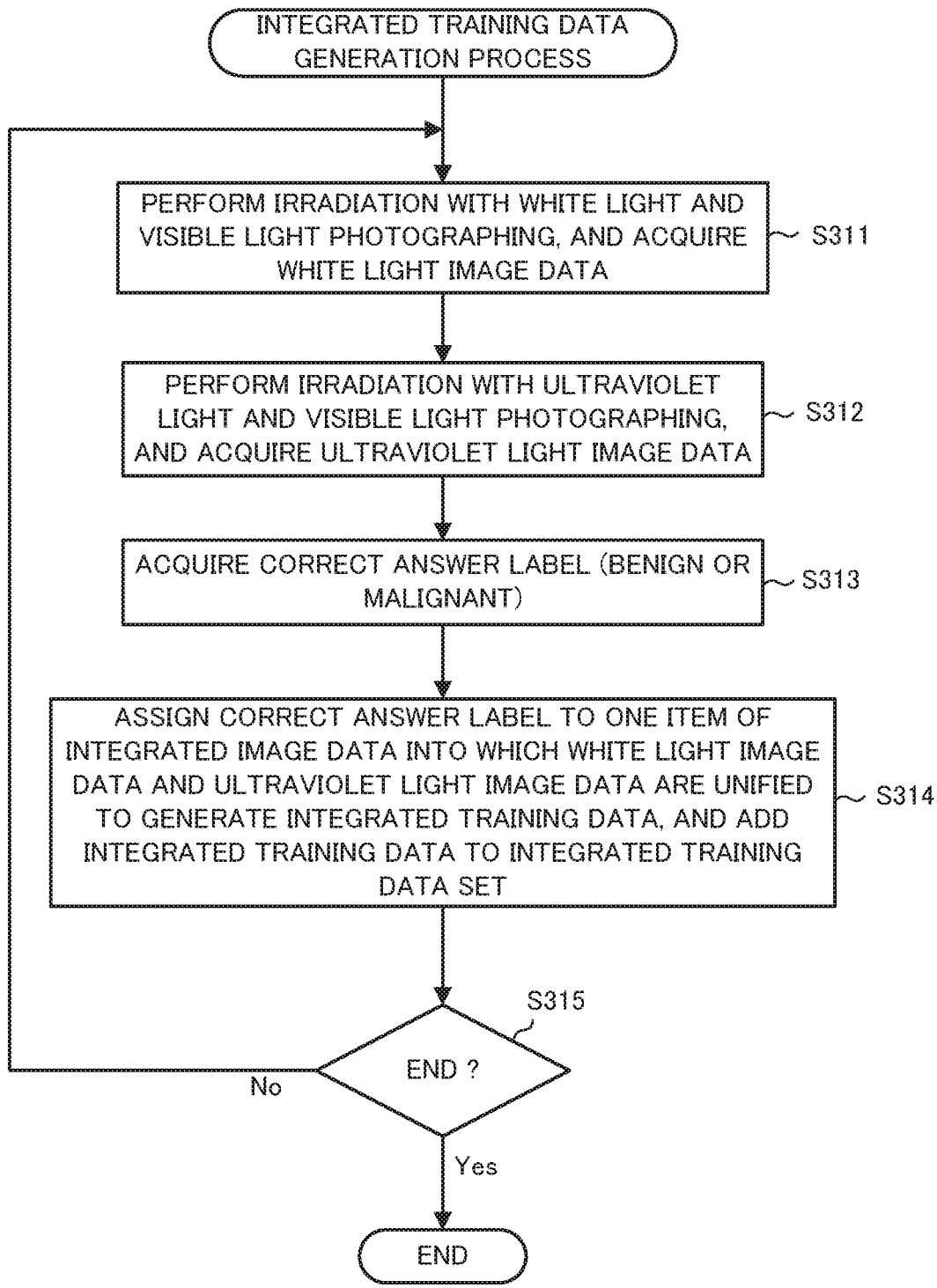
FIG. 8 is a flow chart of an integrated training data generation process according to Variation 1.

First, a controller 10 executes an integrated training data generation process to generate an integrated training data set necessary for supervised machine learning of the CNN of the aliquot identifier (step S501). The integrated image data included in the integrated training data set in Variation 3 is one item of image data including 6-ch RGB, into which the 3-ch RGB of white light image data and the 3-ch RGB of ultraviolet light image data, subjected to high-speed consecutive shooting, are unified. Accordingly, the integrated training data generation process executed in step S501 is similar to the integrated training data generation process (FIG. 8) in Variation 1. In step S501, the controller 10 generates an integrated training data set by generating plural items of integrated training data obtained by assigning a correct answer label to integrated image data. However, in Variation 3, it is not necessary that the visible light photographing of step S311 and the visible light photographing of step S312 are performed by high-speed consecutive shooting in the integrated training data generation process (FIG. 8).

Depending on whether or not the maximum values of the R- or G-values included in ultraviolet light image data included in each integrated training data generated in step S501 are a keratotic plug determination threshold value or more, the controller 10 then assigns a label indicating the existence or non-existence of a keratotic plug to the integrated training data (step S502). For example, assuming that each pixel value (each of R-value, G-value, and B-value) included in each item of image data is 0 or more and 255 or less, and a keratotic plug determination threshold value is 128, a label of "existence of keratotic plug" is assigned to integrated training data including ultraviolet light image data when the maximum value of R-value included is 128 or more, or the maximum value of G-value is 128 or more in the ultraviolet light image data. Assuming that both the maximum values of R- and G-values included in ultraviolet light image data are less than 128, a label of "non-existence of keratotic plug" is assigned to integrated image data including the ultraviolet light image data.

As described above, in the present embodiment, a label of "non-existence of keratotic plug" does not only indicate that a keratotic plug is completely absent but indicates that it is impossible to confirm any keratotic plug on the basis of the pixel values of RGB, and a label of "non-existence of keratotic plug" is assigned when the maximum values of R- and G-values are less than the keratotic plug determination threshold value (when it is impossible to confirm fluorescence) even in the existence of some keratotic plugs. In step S502, it is also acceptable that the whole ultraviolet light image data is not targeted, but a label indicating the existence or non-existence of a keratotic plug is assigned depending on whether or not the maximum values of the R- and G-values of the image data of the portion (non-oncologic portion) other than the affected area in the image are the threshold value keratotic plug determination threshold value or more. In any case, in step S502, when at least one of R-value or G-value that is not less than the keratotic plug determination threshold value is present in targeted ultraviolet light image data, a label of "existence of keratotic plug" is assigned to integrated training data including the ultraviolet light image data.

The keratotic plug determination threshold value and the method of assigning a label in such a case are exemplary. For example, it is also acceptable that the keratotic plug determination threshold value is divided into the threshold values of R- and G-values, and a label of "existence of keratotic plug" may be assigned to integrated training data including ultraviolet light image data when the maximum value of R-value included in the ultraviolet light image data is not less than the keratotic plug determination R threshold value (for example, 80) or the maximum value of G-value is not less than the keratotic plug determination G threshold value (for example, 160). In addition, when the existence or non-existence of a keratotic plug (or the existence of a low level or less of keratotic plug) can be determined, the keratotic plug determination threshold value can be optionally set. Like the benignity and malignancy of an affected area, a label indicating the existence or non-existence of a keratotic plug may be assigned based on the result of diagnosis performed by a doctor regardless of the keratotic plug determination threshold value in the keratotic plug existence/non-existence image learning process.

The controller 10 may determine the existence or non-existence of a keratotic plug by an optional method, which is not limited to the method described above. The controller 10 may assign a label indicating the existence or non-existence of the keratotic plug to each item of integrated training data on the basis of the existence or non-existence of the keratotic plug, determined by the optional method. Step S502 is also referred to as a keratotic plug existence/non-existence determining step.

Then, the controller 10 performs an adoption identifier determination/training process described below using integrated training data to which a label of "existence of keratotic plug" is assigned in step S502 (training data for existence of keratotic plug) among plural items of integrated training data included in the integrated training data set generated in step S501, and performs determination and training of an identifier (or a combination of identifiers) adopted as an identifier for the existence of a keratotic plug by the first final identifier 15 (step S503). The controller 10 executes a keratotic-plug-existence identification process by the identifier (or the combination of identifiers) determined in step S503.

The controller 10 performs the adoption identifier determination/training process described below using integrated training data to which a label of "non-existence of keratotic plug" is assigned in step S502 (training data for non-existence of keratotic plug) among the plural items of integrated training data included in the integrated training data set generated in step S501, performs determination and training of an identifier (or a combination of identifiers) adopted as an identifier for the non-existence of a keratotic plug by the second final identifier 19 (step S504), and ends the keratotic plug existence/non-existence image learning process. The controller 10 executes a keratotic-plug-non-existence identification process by the identifier (or the combination of identifiers) determined in step S504.

Figure 13:
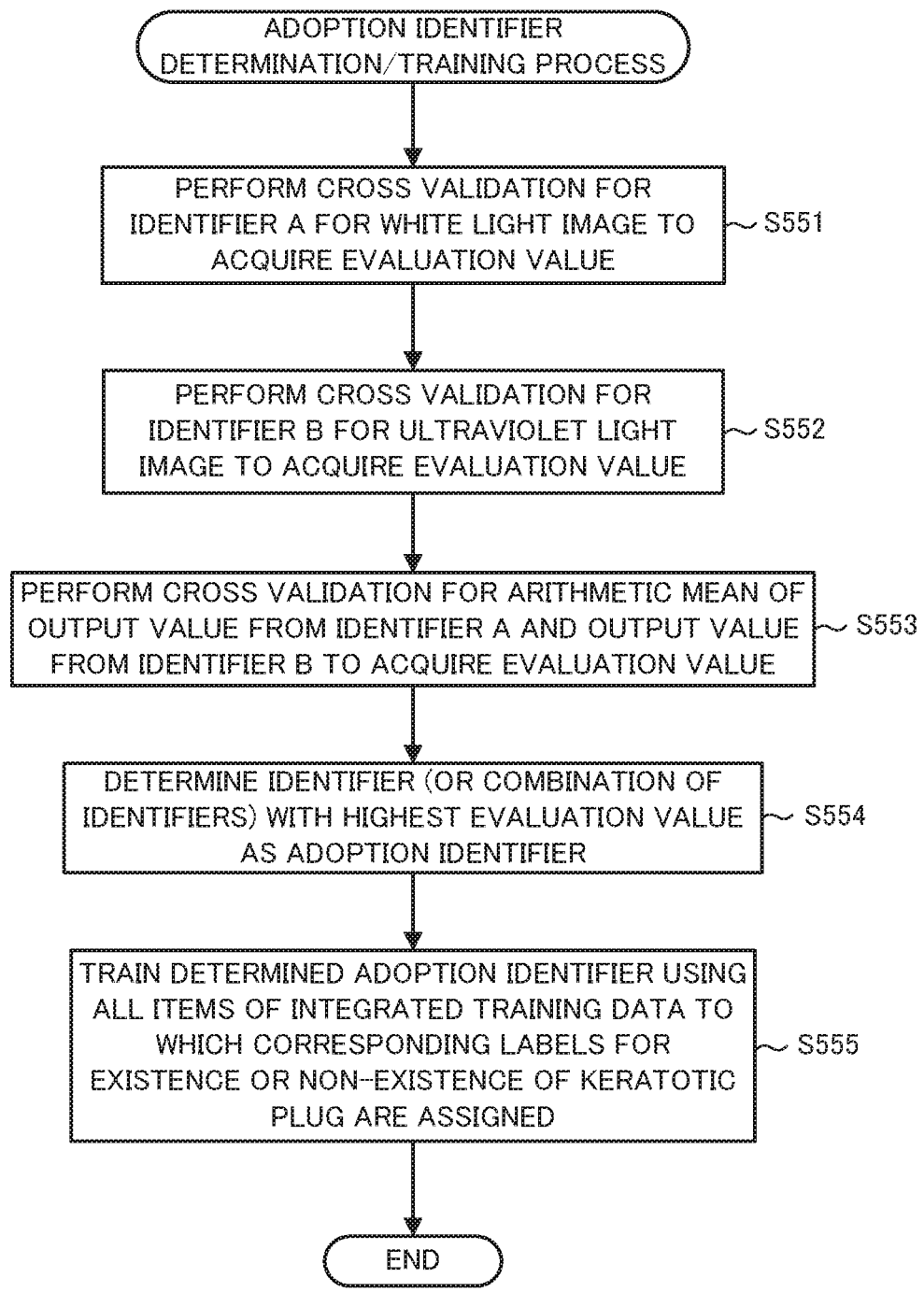
FIG. 13 is a flow chart of an adoption identifier determination/training process according to Variation 3.

The adoption identifier determination/training process executed in step S503 and step S504 will now be described with reference to FIG. 13. In such a case, identifiers targeted for the adoption identifier determination/training process (also referred to as "candidate identifiers" because the identifiers are identifiers as candidates for adoption identifiers) are the first white light image identifier 13 and the first ultraviolet light image identifier 14 in the case of using integrated training data to which the label of "existence of keratotic plug" is assigned, or the second white light image identifier 17 and the second ultraviolet light image identifier 18 in the case of using integrated training data to which the label of "non-existence of keratotic plug" is assigned.

First, the controller 10 subjects "identifier A" for white light image data (the first white light image identifier 13 or the second white light image identifier 17) to cross validation described later, and acquires a first evaluation value which is the evaluation value of the identifier A (step S551). The evaluation value is a value (for example, correct answer rate) that evaluates the correctness of the result of identification performed by the identifier. An evaluation data set used in determination of the evaluation value is an evaluation data aggregate including image data and correct answer labels therefor, and the data structure of the evaluation data set is similar to that of the training data set.

Then, the controller 10 also subjects "identifier B" for ultraviolet light image data (the first ultraviolet light image identifier 14 or the second ultraviolet light image identifier 18) to cross validation, and acquires a second evaluation value which is the evaluation value of the identifier B (step S552).

The controller 10 also subjects "identifier A+identifier B (arithmetic mean of output value from identifier A and output value from identifier B)" to cross validation, and acquires a third evaluation value which is the evaluation value of "identifier A+identifier B" (a combination of the identifier A and the identifier B) (step S553). The process of from step S551 to step S553 is also referred to as "validation step".

Then, the controller 10 determines any one of the identifier A, the identifier B, and a combination of the identifier A and the identifier B, corresponding to the highest evaluation value of the three evaluation values acquired in steps S551 to S553 described above, as an adoption identifier adopted by either the corresponding first final identifier 15 or second final identifier 19 (step S554). Step S554 is also referred to as a determination step. In such a case, an adoption identifier adopted as an identifier for the existence of a keratotic plug by the first final identifier 15 is determined in the case of using integrated training data to which the label of "existence of keratotic plug" is assigned. An adoption identifier adopted as an identifier for the non-existence of a keratotic plug by the second final identifier 19 is determined in the case of using integrated training data to which the label of "non-existence of keratotic plug" is assigned.

The adoption identifiers are trained using all the items of integrated training data (to which corresponding labels for the existence or non-existence of a keratotic plug are assigned) (step S555), and the adoption identifier determination/training process is ended.

The cross validation performed in steps S551 to S553 described above will now be described with reference to FIG. 14. Commonly, in n-fold cross validation, 1/n of the whole training data set is used as an evaluation data set, and (n−1)/n as the remainder is used as a transitory training data set in the case of validation with the evaluation data set (in the case of determination of the evaluation value). The upper diagram of FIG. 14 illustrates an example in the case of n=3, that is, an example of three-fold cross validation.

A method of acquiring an evaluation value from the whole training data set will now be described by taking the identifier A as an example. In acquisition of an evaluation value, however, an identification result (output from identifier) is given as a probability in the present embodiment, and therefore, it is impossible to simply compare a correct answer label and an identification result. Thus, the evaluation value is set so that the evaluation value is increased with decreasing a difference between a numeral value (correct answer value) into which a correct answer label is converted and an output (probability) from an identifier.

First, the identifier A is trained using the initial ⅔ (training data) of training data. An output from the identifier A in the case of inputting the remaining ⅓ (evaluation data) of the training data into the trained identifier A is compared with the numeral value (correct answer value) into which the correct answer label (assigned to each item of evaluation data) is converted. The evaluation value 1 is set so that the evaluation value 1 becomes a value that is increased with decreasing a difference between the output from the identifier A and the correct answer value.

In the present embodiment, an output from the identifier A is the probability (0.0 or more and 1.0 or less) of the malignancy of an affected area. Therefore, when correct answer labels are converted into numeral correct answer values, correct answer values, for example, in cases in which correct answer labels are "benign" and "malignant" can be defined as 0.0 and 1.0, respectively. Accordingly, "difference between output from identifier A and correct answer value" is (output from identifier A−0.0) in a case in which the correct answer label is "benign" or (1.0−output from identifier A) in a case in which the correct answer label is "malignant". A value (total sum of differences) obtained by addition of "differences between outputs from identifier A and correct answer values" in the case of inputting all the respective items of evaluation data into the identifier A is determined, and the inverse number of the value (total sum of differences) is regarded as the evaluation value 1.

Then, the identifier A is trained using, as training data, the initial ⅓ and end ⅓ of the training data included in the training data set, and an evaluation value obtained by evaluating the identifier A trained using the middle ⅓ of the training data as evaluation data is regarded as an evaluation value 2. The identifier A is trained using, as training data, the end ⅔ of the training data included in the training data set, and an evaluation value obtained by evaluating the identifier A trained using the initial ⅓ of the Training Data as Evaluation data is regarded as an evaluation value 3. Methods of computing the evaluation value 2 and the evaluation value 3 are similar to the above-described method of computing the evaluation value 1. The total (or the average value or the like is also acceptable) of the evaluation value 1, the evaluation value 2, and the evaluation value 3 is regarded as the evaluation value (first evaluation value) of the identifier A, obtained from the whole training data set used in such a case.

The method of computing the evaluation value (first evaluation value) by taking the identifier A as an example has been described above. The evaluation value (second evaluation value) of the identifier B can also be similarly determined. The evaluation value (third evaluation value) of the combination (identifier A+identifier B) of the identifier A and the identifier B can be determined as described below.

First, each of the identifier A and the identifier B is trained using the initial ⅔ of training data as training data. The average value of the output from the identifier A and the output from the identifier B in the case of inputting the remaining ⅓ (evaluation data) of the training data into each of the trained identifier A and the trained identifier B is compared with the numeral value (correct answer value) into which the correct answer label (assigned to each item of evaluation data) is converted. The evaluation value 1 is set so that the evaluation value 1 is a value that is increased with decreasing the difference between the correct answer value and the average value of the output from the identifier A and the output from the identifier B. The evaluation value 2 and the evaluation value 3 are determined in a similar manner, the total (or the average value or the like is also acceptable) of the evaluation value 1, the evaluation value 2, and the evaluation value 3 is regarded as the evaluation value (third evaluation value) of the combination (identifier A+identifier B) of the identifier A and the identifier B, obtained from the whole training data set used in such a case.

In steps S551 to S553 of the adoption identifier determination/training process described above (FIG. 13), the evaluation value obtained from the whole training data set is acquired for each of three patterns of the identifier A, the identifier B, and identifier A+identifier B (the arithmetic mean of the output value from the identifier A and the output value from the identifier B) (identifier or combination of identifiers) in such a manner as described above. In step S554, the pattern with the highest evaluation value (identifier or combination of identifiers) is determined as an adoption identifier (that is, the identifier for the existence of a keratotic plug or the identifier for the non-existence of a keratotic plug). In step S555, the determined adoption identifier is trained using all the items of integrated training data included in the integrated training data set.

Figure 12:
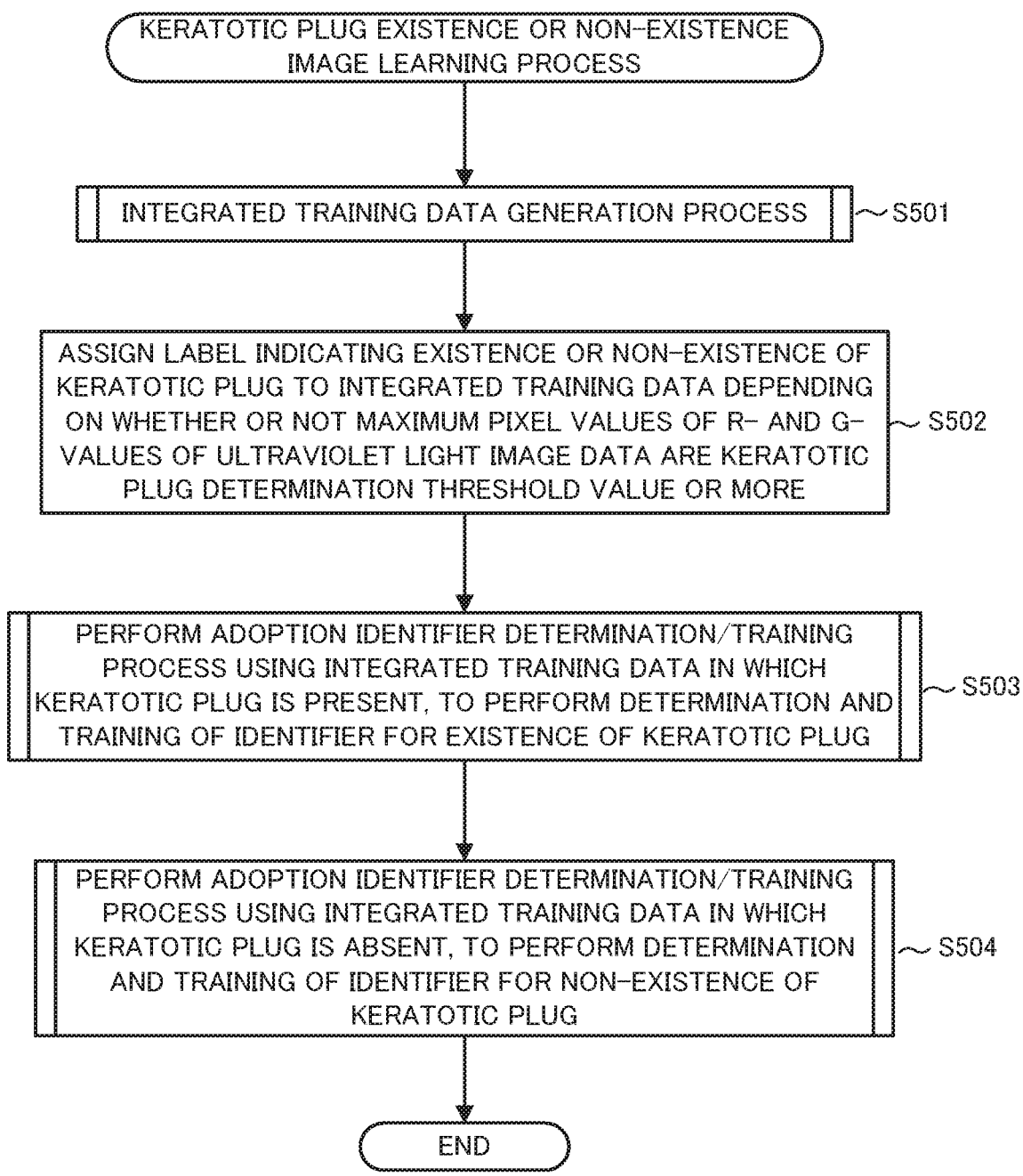
FIG. 12 is a flow chart of an image learning process for the existence or non-existence of a keratotic plug according to Variation 3.

However, the training data set in FIG. 14 is a training data set including all the items of integrated training data to which the label of "existence of keratotic plug" is assigned in a case in which the adoption identifier determination/training process (FIG. 13) is called from step S503 of the keratotic plug existence/non-existence image learning process (FIG. 12). The training data set in FIG. 14 is a training data set including all the items of integrated training data to which the label of "non-existence of keratotic plug" is assigned in a case in which the adoption identifier determination/training process (FIG. 13) is called from step S504 of the keratotic plug existence/non-existence image learning process (FIG. 12).

For example, when the training data set includes all the items of integrated training data to which the label of "existence of keratotic plug" is assigned, and the pattern of the identifier with the highest evaluation value is "identifier A+identifier B (arithmetic mean of output value from identifier A and output value from identifier B)", it is determined that the first final identifier 15 adopts "arithmetic mean of output value from first white light image identifier 13 and output value from first ultraviolet light image identifier 14" as an output from an identifier for the existence of a keratotic plug, and the controller 10 trains each of the first white light image identifier 13 and the first ultraviolet light image identifier 14 using all the items of integrated image data (image data including 6-ch RGB) to which the label of "existence of keratotic plug" included in the integrated training data set is assigned.

When the training data set includes all the items of integrated training data to which the label of "non-existence of keratotic plug" is assigned, and the pattern of the identifier with the highest evaluation value is "identifier A", it is determined that the second final identifier 19 adopts "second white light image identifier 17" as the identifier for the non-existence of a keratotic plug, and the controller 10 trains the second white light image identifier 17 using all the items of integrated training data to which the label of "non-existence of keratotic plug" is assigned, included in the integrated training data set. As described above, the training data set includes two kinds of data to which the label of "existence of keratotic plug" is assigned (integrated training data for existence of keratotic plug) and data to which the label of "non-existence of keratotic plug" is assigned (integrated training data for non-existence of keratotic plug), and the pattern of the identifier with the highest evaluation value, of the three patterns of the identifiers ("identifier A", "identifier B," and "identifier A+identifier B"), is trained for each of the integrated training data for the existence of a keratotic plug and the integrated training data for the non-existence of a keratotic plug.

In the descriptions described above, the output value in a case in which the pattern of the identifier is "identifier A+identifier B" is set at "arithmetic mean of output value from identifier A and output value from identifier B". However, the output value need not be limited to the arithmetic mean. It is also acceptable that the controller 10 also adds, for example, plural patterns of weighted means in which various weights are used as candidates for cross validation, performs cross validation of all the patterns, and determines the identifier of the pattern with the highest evaluation value (or a combination of identifiers with various weighted means) as an adopted identifier. It is not necessary to limit candidate identifiers per se to two of the identifier A and the identifier B. Like the identifier A or the identifier B, for example, another identifier such as an identifier that inputs an image subjected to pretreatment of cropping (cutting) the periphery of the lesion region of an affected area to normalize the size thereof, to thereby identify the affected area, or an identifier that inputs an image subjected to pretreatment of subjecting an image obtained by photographing an affected area to edge enhancement, to thereby identify the affected area may be added to candidate identifiers to perform cross validation. Among all the candidate identifiers and the combinations of the candidate identifiers, the identifier with the highest evaluation value obtained by cross validation may be determined as the adoption identifier adopted as the identifier that identifies the affected area.

The CNNs of the first white light image identifier 13, the first ultraviolet light image identifier 14, the second white light image identifier 17, and the second ultraviolet light image identifier 18 are trained by the adoption identifier determination/training process and the keratotic plug existence/non-existence image learning process, described above. In the keratotic plug existence/non-existence image learning process, it is possible to divide training data depending on the existence or non-existence of a keratotic plug and to train each identifier. Therefore, the identifier for the existence of a keratotic plug can be trained only with image data with a keratotic plug, and the identifier for the non-existence of a keratotic plug can be trained only with image data without a keratotic plug. Thus, the training can be efficiently performed. In the adoption identifier determination/training process, identifiers (or a combination of identifiers) considered to have the highest identification performance can be determined as adoption identifiers (first final identifier 15 and second final identifier 19) by performing cross validation.

Figure 15:
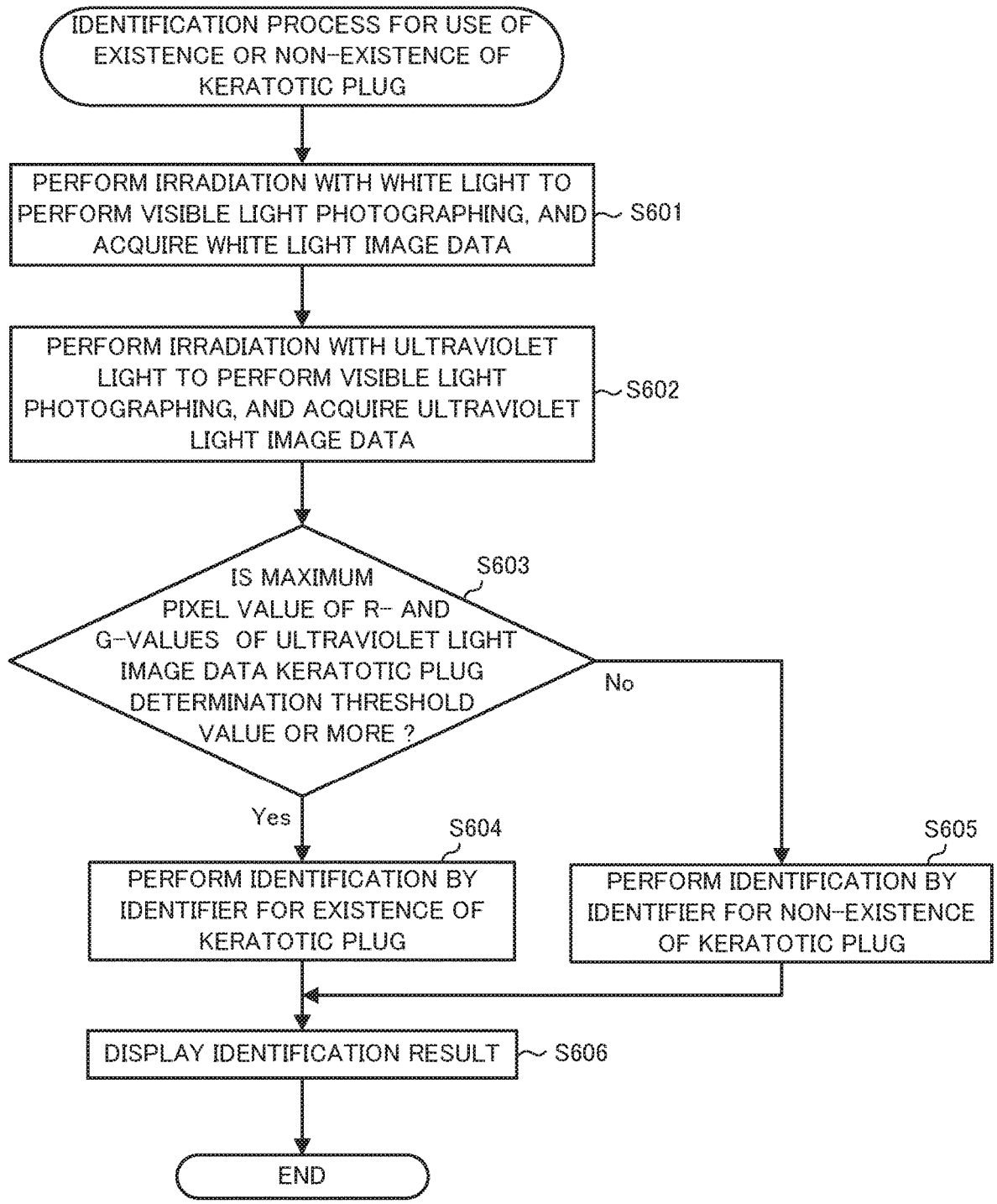
FIG. 15 is a flow chart of an identification process for use of the existence or non-existence of a keratotic plug according to Variation 3.

The identification process for use of the existence or non-existence of a keratotic plug, in which the benignity or malignancy of the (unknown) affected area targeted for identification is identified (inferred) after such training, will now be described with reference to FIG. 15.

The processes of step S601 and step S602 are similar to the respective processes of step S401 and step S402 of the identification process (FIG. 9) according to Variation 1, and therefore, the descriptions thereof are omitted. In Variation 3, however, the visible light photographing of step S601 and the visible light photographing of step S602 need not be performed by high-speed consecutive shooting.

The controller 10 determines whether or not the maximum values of the R- and G-values included in ultraviolet light image data acquired in step S602 are a keratotic plug determination threshold value or more (step S603). Step S603 is also referred to as a keratotic plug existence/non-existence determining step. The controller 10 executes a keratotic-plug-existence process in step S603.

When the maximum values of the R- and G-values included in the ultraviolet light image data are the keratotic plug determination threshold value or more (step S603; Yes), the first final identifier 15 identifies the affected area by the identifier for the existence of a keratotic plug, determined in the keratotic plug existence/non-existence image learning process described above (step S604). For example, when the identifier for the existence of a keratotic plug is "identifier A+identifier B (arithmetic mean of output value from identifier A and output value from identifier B)", the first final identifier 15 obtains a final identification result by the arithmetic mean of the output value from the first white light image identifier 13, obtained by inputting the white light image data that acquired in step S601 into the first white light image identifier 13, and the output value from the first ultraviolet light image identifier 14, obtained by inputting the ultraviolet light image data acquired in step S602 into the first ultraviolet light image identifier 14.

In contrast, when the maximum values of the R- and G-values included in the ultraviolet light image data are less than the keratotic plug determination threshold value (step S603; No), the second final identifier 19 identifies the affected area by the identifier for the non-existence of a keratotic plug, determined in the keratotic plug existence/non-existence image learning process (step S605). For example, when the identifier for the non-existence of a keratotic plug is "identifier A", the second final identifier 19 obtains a final identification result by the output value from the second white light image identifier 17, obtained by inputting the white light image data acquired in step S601 into the second white light image identifier 17.

The controller 10 displays, on an outputter 33, the final identification result based on the first final identifier 15 or the second final identifier 19 (step S606), and ends the identification process for use of the existence or non-existence of a keratotic plug.

The method of determining the existence or non-existence of a keratotic plug in step S603 is exemplary. Like step S502 of the keratotic plug existence/non-existence image learning process (FIG. 12), the keratotic plug determination threshold value divided into a keratotic plug determination R threshold value (for example, 80) and a keratotic plug determination G threshold value (for example, 160) may be set, or the controller 10 may determine the existence or non-existence of a keratotic plug by an optional method which is not limited to the method described above.

In the identification process for use of the existence or non-existence of a keratotic plug as described above, proper use of an identifier based on the existence or non-existence of a keratotic plug, which is relatively easily identified, enables the affected area to be identified using an identifier optimized depending on the existence or non-existence of the keratotic plug, and therefore, identification performance can be improved in comparison with conventional identification (based on only white light image data).

(Variation of Variation 3)

In Variation 3, training data is classified into training data for the existence of a keratotic plug and training data for the non-existence of a keratotic plug, and the dedicated identifiers (the identifier for the existence of a keratotic plug and the identifier for the non-existence of a keratotic plug) are trained using the items of the classified training data, respectively. However, a method of classifying the training data is not limited to the classification based on the existence or non-existence of a keratotic plug. For example, as a Variation of Variation 3, an embodiment can also be conceivable in which training data is classified into training data for the face and the scalp, and training data for the whole body, and dedicated identifiers (an identifier for the face and the scalp, and an identifier for the whole body) are trained using the items of the classified training data, respectively.

In Variation 3, the label for the existence or non-existence of a keratotic plug, indicating the existence or non-existence of a keratotic plug, is assigned to each item of the integrated training data. In the Variation of Variation 3, however, training data is classified into training data for the face and the scalp (training data in which the site of an affected area is the face or the scalp) and training data for the whole body (training data without depending on the site of an affected area) by assigning a site label (for example, "scalp" "face", or the like) indicating the site of an affected area in the body, captured in an image, to each item of integrated training data.

The identifier for the face and the scalp, and the identifier for the whole body are trained by a process similar to the keratotic plug existence/non-existence image learning process (FIG. 12) (however, training data with a site label of "scalp" or "face" is used instead of training data of "existence of keratotic plug", and all items of training data (that are not subjected to site separation) are used instead of training data of "non-existence of keratotic plug"; hereinafter, the process is referred to as "training process with use of site").

A keratotic plug is more likely to exist particularly in the face and the scalp in the sites of the body (a keratotic plug hardly exists in the other sites of the body than the face and the scalp). Therefore, when a keratotic plug exists in an image obtained by photographing an affected area, the affected area is more likely to be an affected area existing in the face or the scalp. Accordingly, in the Variation of Variation 3, an affected area can be identified by a process similar to the identification process for use of the existence or non-existence of a keratotic plug (FIG. 15) (however, identification is performed in the identifier for the face and the scalp in step S604, and identification is performed in the identifier for the whole body in step S605; hereinafter, the process is referred to as "identification process with use of site").

In the Variation of Variation 3, an identifier dedicated to each site can be trained on the basis of the site label regardless of the existence or non-existence of a keratotic plug in the training process using a site as described above, and therefore, the training data of the face and the scalp in the case of detecting no keratotic plug can also be used for the training of the identifier for the face and the scalp. In the above-described identification process using a site, when a keratotic plug is detected (because a keratotic plug often exists only in the face or the scalp), identification performance can be further improved by using the identifier for the face and the scalp, dedicated to use in the face and the scalp.

Other Variations

In the embodiment and Variations described above, execution of a program that implements an identifier based on CNN by the controller 10 allows the controller 10 to also function as the first white light image identifier 13, the first ultraviolet light image identifier 14, the integrated image identifier 16, the second white light image identifier 17, or the second ultraviolet light image identifier 18, without limitation thereto. The identification apparatuses 100, 101, 102, and 103 may include a device (for example, graphics processing unit (GPU), dedicated integrated circuit (IC), or the like) different from the controller 10, and the function of the first white light image identifier 13, the first ultraviolet light image identifier 14, the integrated image identifier 16, the second white light image identifier 17, or the second ultraviolet light image identifier 18 may be implemented by the device.

The embodiment and Variations described above can be combined as appropriate. For example, it is also acceptable that Variation 3 is combined with Variation 1 or Variation 2, and identification is performed using the integrated image identifier 16 in which one item of 6-ch integrated image data into which the 3-ch RGB of white light image data and the 3-ch RGB of ultraviolet light image data are unified, or one item of 5-ch Integrated image data into which the 3-ch RGB of white light image data and the 2-ch RG of ultraviolet light image data are unified is used as input data, instead of or in addition to "identifier A+identifier B (arithmetic mean of output value from identifier A and output value from identifier B)".

In such a case, each of a first integrated image identifier for identifying an affected area captured in image data with a keratotic plug and a second integrated image identifier for identifying an affected area captured in image data without a keratotic plug is also prepared in the integrated image identifier 16. In step S553 of the adoption identifier determination/training process in which the integrated training data with a keratotic plug is used, the evaluation value of the first integrated image identifier is determined. In step S553 of the adoption identifier determination/training process in which the integrated training data without a keratotic plug is used, the evaluation value of the second integrated image identifier is determined.

Figure 5:
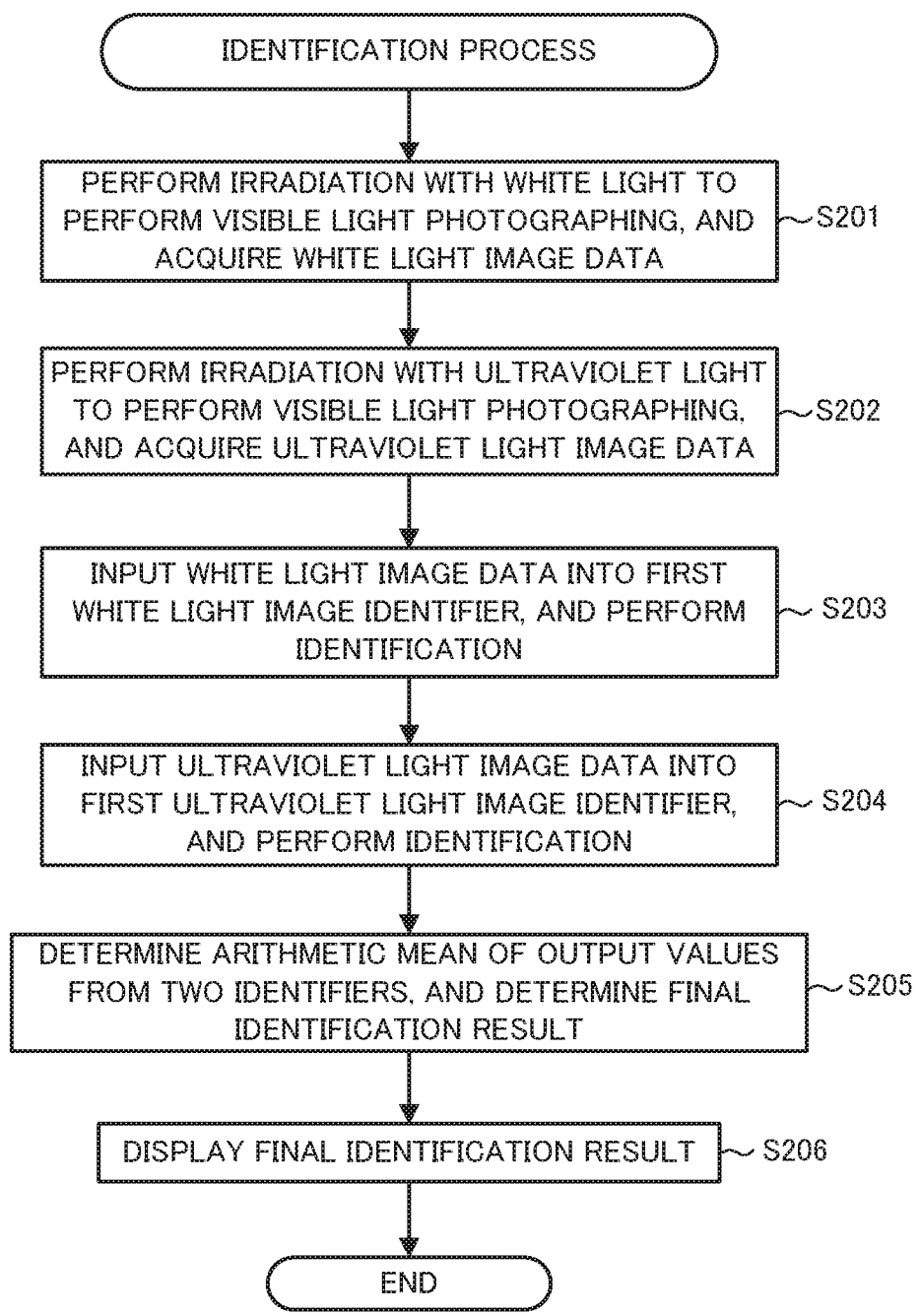
FIG. 5 is a flow chart of an identification process according to Embodiment 1.

In the identification apparatus 100 according to Embodiment 1, it is also acceptable that the adoption identifier determination/training process (FIG. 13) of Variation 3 is performed after the identifier training process (FIG. 3), and the result of identification with the pattern of the identifier with the highest evaluation value is regarded as an identification result in step S205 of the identification process (FIG. 5).

The embodiment and the Variations have been described above using an RGB color space as a color space expressing the colors of image data, and using R-value, G-value, and B-value as color components. However, the color space is not limited to the RGB color space. For example, a YUV color space or a Lab color space may be used.

In the embodiment and Variations described above, it has been described that the irradiator 31 emits ultraviolet light as the second irradiation light. However, the ultraviolet light is exemplary. The second irradiation light may be optional light as long as the light allows a keratotic plug and the like to show fluorescent reaction. For example, the irradiator 31 may perform irradiation with the light (for example, light having a wavelength of 410 nm to 470 nm, preferably 440 nm or less), closer to ultraviolet light, of visible light, as the second irradiation light.

Each function of the identification apparatuses 100, 101, 102, and 103 can also be implemented by a computer such as a usual personal computer (PC). Specifically, in the embodiment described above, it has been described that a program for the identification process performed by the identification apparatus 100, 101, 102, or 103, or the like is stored in the ROM of the storage 20 in advance. However, it is also acceptable to configure a computer that can implement each function described above by distributing a non-transitory computer-readable recording medium, such as a flexible disk, a compact disc read only memory (CD-ROM), a digital versatile disc (DVD), a magneto-optical disc (MO), a memory card, or a universal serial bus (USB) memory, in which the program is stored, and by allowing the computer to read and install the program.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. An identification apparatus comprising:
a processor; and
a memory configured to store a program to be executed by the processor,
wherein the processor is configured to:
acquire first image data obtained by capturing of an image of an affected area included in a skin or a mucosa by receiving first reception light, the first reception light being reflection light reflected from the affected area irradiated with first irradiation light including white light,
acquire second image data obtained by capturing of an image of the affected area by receiving second reception light, the second reception light being light including light generated by fluorescent reaction in the affected area irradiated with second irradiation light, and the second irradiation light including light that allows the affected area to show fluorescent reaction when the affected area is irradiated with the light, and
identify the affected area based on R-, G-, and B-values of the first image data and R- and G-values of the second image data.

2. The identification apparatus according to claim 1, wherein the processor is configured to identify the affected area according to a model in which machine learning is performed using input data based on the first image data and the second image data as an input and a result of identifying the affected area as an output.

3. The identification apparatus according to claim 2, wherein the processor identifies the affected area using an identifier that outputs a result of identifying the affected area when integrated image data that is integrated data of the first image data and the second image data is input.

4. The identification apparatus according to claim 2, wherein the processor is configured to:

execute a first identification process of identifying, based on the acquired first image data, whether or not the affected area is malignant, execute a second identification process of identifying, based on the acquired second image data, whether or not the affected area is malignant, and identify the affected area based on an identification result obtained in the first identification process and an identification result obtained in the second identification process.

5. The identification apparatus according to claim 2, wherein the processor is configured to:

execute a keratotic plug existence/non-existence determining process of determining, based on the second image data, whether or not there is a keratotic plug in the affected area, execute a keratotic-plug-existence identification process of identifying the affected area based on the first image data and the second image data for which a determination that there is a keratotic plug in the affected area is made in the keratotic plug existence/non-existence determining process, execute a keratotic-plug-non-existence identification process of identifying the affected area based on the first image data and the second image data for which a determination that there is no keratotic plug in the affected area is made in the keratotic plug existence/non-existence determining process, identify the affected area based on an identification result obtained in the keratotic-plug-existence identification process when a determination that there is a keratotic plug in the affected area is made for the second image data in the keratotic plug existence/non-existence identification process, and identify the affected area based on an identification result obtained in the keratotic-plug-non-existence identification process when a determination that there is no keratotic plug in the affected area is made for the second image data in the keratotic plug existence/non-existence identification process.

6. The identification apparatus according to claim 5, wherein in the keratotic plug existence/non-existence identification process, existence or non-existence of a keratotic plug in the affected area is determined based on whether or not maximum values of at least one of the R- and G-values included in the second image data are a keratotic plug determination threshold value or more.

7. The identification apparatus according to claim 2, wherein a time difference between an image capturing timing for the first image data and an image capturing timing for the second image data is equal to or less than a consecutive shooting reference time.

8. An identifier training method for an identification apparatus, the identifier training method comprising:

acquiring first image data obtained by capturing of an image of an affected area included in a skin or a mucosa by receiving first reception light, the first reception light being reflection light reflected from the affected area irradiated with first irradiation light including white light;

acquiring second image data obtained by capturing of an image of the affected area by receiving second reception light, the second reception light being light including light generated by fluorescent reaction in the affected area irradiated with second irradiation light, and the second irradiation light including light that allows the affected area to show fluorescent reaction when the affected area is irradiated with the light; and training, based on R-, G-, and B-values of the first image data and R- and G-values of the second image data, an identifier that identifies the affected area.

9. The identifier training method according to claim 8, wherein a time difference between an image capturing timing for the first image data and an image capturing timing for the second image data is equal to or less than a consecutive shooting reference time.

10. The identifier training method according to claim 8, further comprising:

determining, based on the second image data, whether or not there is a keratotic plug in the affected area, wherein the training of the identifier includes:

training a keratotic-plug-existence identifier that identifies the affected area for which a determination that there is a keratotic plug is made, based on the first image data and the second image data for which a determination that there is a keratotic plug in the affected area is made in the determining, and training a keratotic-plug-non-existence identifier that identifies the affected area for which a determination that there is no keratotic plug is made, based on the first image data and the second image data for which a determination that there is no keratotic plug in the affected area is made in the determining.

11. The identifier training method according to claim 10, wherein the determining includes determining existence or non-existence of a keratotic plug in the affected area based on whether or not maximum values of at least one of the R- and G-values included in the second image data are a keratotic plug determination threshold value or more.

12. The identifier training method according to claim 8, further comprising:

acquiring an evaluation value that is a value obtained by evaluating correctness of identification results of each of candidate identifiers and a combination of the candidate identifiers; and determining, based on the evaluation values of the candidate identifiers and the combination of the candidate identifiers acquired in the acquiring of the evaluation value, an adoption identifier to be adopted as an identifier that identifies the affected area from among each of the candidate identifiers and the combination of the candidate identifiers, wherein the training of the identifier includes training the adoption identifier determined in the determining of the adoption identifier.

13. The identifier training method according to claim 12, wherein:

the acquiring of the evaluation value includes acquiring a first evaluation value that is an evaluation value of a first identifier that identifies the affected area based on the first image data, a second evaluation value that is an evaluation value of a second identifier that identifies the affected area based on the second image data, and a third evaluation value that is an evaluation value of identification of the affected area based on an average value of an output value of the first identifier and an output value of the second identifier, and the determination of the adoption identifier includes determining the adoption identifier based on a maximum value of the first evaluation value, the second evaluation value, and the third evaluation value.

14. An identification method for an identification apparatus, the identification method comprising:

acquiring first image data obtained by capturing of an image of an affected area included in a skin or a mucosa by receiving first reception light, the first reception light being reflection light reflected from the affected area irradiated with first irradiation light including white light;

acquiring second image data obtained by capturing of an image of the affected area by receiving second reception light, the second reception light being light including light generated by fluorescent reaction in the affected area irradiated with second irradiation light, the second irradiation light including light that allows the affected area to show fluorescent reaction when the affected area is irradiated with the light; and identifying the affected area based on R-, G-, and B-values of the first image data and R- and G-values of the second image data.

15. A non-transitory computer-readable recording medium that stores a program for allowing a computer of an identification apparatus to execute processing comprising:

acquiring first image data obtained by capturing of an image of an affected area included in a skin or a mucosa by receiving first reception light, the first reception light being reflection light reflected from the affected area irradiated with first irradiation light including white light;

acquiring second image data obtained by capturing of an image of the affected area by receiving second reception light, the second reception light being light including light generated by fluorescent reaction in the affected area irradiated with second irradiation light, the second irradiation light including light that allows the affected area to show fluorescent reaction when the affected area is irradiated with the light; and identifying the affected area based on R-, G-, and B-values of the first image data and R- and G-values of the second image data.

* * * * *